(12) United States Patent
Schmitter et al.

(10) Patent No.: US 10,247,803 B2
(45) Date of Patent: Apr. 2, 2019

(54) SYSTEMS AND METHODS FOR DESIGNING MAGNETIC RESONANCE IMAGING RADIO FREQUENCY PULSES THAT ARE ROBUST AGAINST PHYSIOLOGICAL MOTION ERRORS

(71) Applicant: Regents of the University of Minnesota, Minneapolis, MN (US)

(72) Inventors: Sebastian Schmitter, Minneapolis, MN (US); Pierre-Francois van de Moortele, Minneapolis, MN (US); Xiaoping Wu, Minneapolis, MN (US); Kamil Ugurbil, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 349 days.

(21) Appl. No.: 14/696,099

(22) Filed: Apr. 24, 2015

(65) Prior Publication Data
US 2015/0309147 A1   Oct. 29, 2015

Related U.S. Application Data

(60) Provisional application No. 61/984,268, filed on Apr. 25, 2014.

(51) Int. Cl.
*G01R 33/567* (2006.01)
*A61B 5/055* (2006.01)
(Continued)

(52) U.S. Cl.
CPC ............ *G01R 33/567* (2013.01); *A61B 5/055* (2013.01); *G01R 33/246* (2013.01);
(Continued)

(58) Field of Classification Search
CPC .............. G01R 33/567; G01R 33/5659; G01R 33/565; G01R 33/56509; G01R 33/5676;
(Continued)

(56) References Cited

U.S. PATENT DOCUMENTS 7,800,368 B2 *   9/2010   Vaughan .............. G01R 33/583
                                                                    324/318
7,826,886 B2 *  11/2010   Jhooti ................ G01R 33/5676
                                                                    324/309
(Continued)

FOREIGN PATENT DOCUMENTS

WO        2013105006 A1      7/2013

OTHER PUBLICATIONS

Van de Moortele et al. "Respiration-Induced B0 Fluctuations and Their Spatial Distribution in the Human Brain at 7 Tesla". Magn Reson Med 47:888-895 (2002).*
(Continued)

*Primary Examiner* — Angela M Hoffa
(74) *Attorney, Agent, or Firm* — Quarles & Brady LLP

(57) ABSTRACT

Systems and methods for designing and/or using radio frequency ("RF") pulses for in-vivo MRI applications, where the RF pulses are robust against errors due to physiological motion of organs during the respiratory cycle. For example, RF pulses are designed based on multi-channel B1+ maps correlated to different positions of the respiratory cycle.

7 Claims, 16 Drawing Sheets
(12 of 16 Drawing Sheet(s) Filed in Color)

(51) Int. Cl.
*G01R 33/44* (2006.01)
*G01R 33/561* (2006.01)
*G01R 33/563* (2006.01)
*G01R 33/565* (2006.01)
*G01R 33/24* (2006.01)
*G01R 33/54* (2006.01)
*A61B 5/00* (2006.01)
*A61B 5/113* (2006.01)

(52) U.S. Cl.
CPC ......... *G01R 33/443* (2013.01); *G01R 33/543* (2013.01); *G01R 33/565* (2013.01); *G01R 33/5612* (2013.01); *G01R 33/5659* (2013.01); *G01R 33/5676* (2013.01); *G01R 33/56308* (2013.01); *G01R 33/56509* (2013.01); *A61B 5/113* (2013.01); *A61B 5/721* (2013.01); *A61B 5/7289* (2013.01); *G01R 33/5673* (2013.01); *G01R 33/56325* (2013.01); *G01R 33/56563* (2013.01)

(58) Field of Classification Search
CPC ............ G01R 33/56308; G01R 33/443; G01R 33/246; G01R 33/5673; G01R 33/56563; G01R 33/56325; G01R 33/5612; G01R 33/543; A61B 5/055; A61B 5/721; A61B 5/7289; A61B 5/113
See application file for complete search history.

(56) References Cited

U.S. PATENT DOCUMENTS

| | | | | |
|---|---|---|---|---|
| 7,945,305 | B2* | 5/2011 | Aggarwal | G01R 33/5673 600/407 |
| 8,085,044 | B2* | 12/2011 | Setsompop | G01R 33/246 324/309 |
| 8,138,759 | B2* | 3/2012 | Greiser | G01R 33/3875 324/309 |
| 8,185,187 | B2* | 5/2012 | Xu | A61B 5/055 600/413 |
| 8,564,290 | B2* | 10/2013 | Tomoda | G01R 33/5676 324/306 |
| 8,653,818 | B2* | 2/2014 | Adalsteinsson | G01R 33/5612 324/307 |
| 9,977,106 | B2* | 5/2018 | Nehrke | G01R 33/50 |
| 2012/0256626 | A1* | 10/2012 | Adalsteinsson | G01R 33/5612 324/309 |
| 2013/0063143 | A1* | 3/2013 | Adalsteinsson | G01R 33/5612 324/307 |
| 2013/0197347 | A1* | 8/2013 | Moghari | A61B 5/7207 600/410 |
| 2014/0037171 | A1* | 2/2014 | Bhat | G06T 11/003 382/131 |
| 2015/0002149 | A1 | 1/2015 | Nehrke et al. | |
| 2015/0323637 | A1* | 11/2015 | Beck | G01R 33/4828 600/410 |
| 2017/0307710 | A1* | 10/2017 | Boulant | G01R 33/5612 |

OTHER PUBLICATIONS

Setsompop et al. "Magnitude Least Square Optimization for Parallel Radio Frequency Excitation Design Demonstrated at 7 Tesla with Eight Channels". Magn Reson Med 59(4): 908-915 (Apr. 2008).*
Homann et al. "Specific Absorption Rate Reduction in Parallel Transmission by k-Space Adaptive Radiofrequency Pulse Design". Magn Reson Med 65:350-357 (2011).*
Wu et al. "Simultaneous multi-slice multi-band parallel RF excitation with independent slice-specific transmit B1 homogenization". Magn Reson Med 70(3): 630-638 (Sep. 2013).*
Metzger et al. "Dynamically Applied B1+ Shimming Solution for Non-Contrast Enhanced Renal Angiography at 7.0 Tesla". Magn Reson Med 69(1): 114-126 (Jan. 2013).*
Schmitter et al. "Cardiac Imaging at 7T: Single- and Two-Spoke RF Pulse Design with 16-channel Parallel Excitation". Magn Reson Med 70(5): 1210-1219 (Nov. 2013).*
Guerin et al. "Design of parallel transmission pulses for simultaneous multi-slice with explicit control for peak power and local specific absorption rate". Magn Reson Med 73(5): 1946-1953 (May 2015).*
Schmitter et al. "Design of PTX RF Pulses Robust Against Respiration in Cardiac MRI at 7 Tesla". Magn Reson Med 74(5):1291-1305 (Nov. 2015).*
Harvey et al. "MultiTransmit parallel RF transmission technology." Philips Healthcare. Aug. 2009, 16 pages.*
Kay Nehrke et al., Free-Breathing Abdominal B1 Mapping at 3T Using the DREAM Approach, Proc. Intl. Soc. Mag. Reson. Med. 20 (2012), p. 3356.

* cited by examiner

Spoke Placement
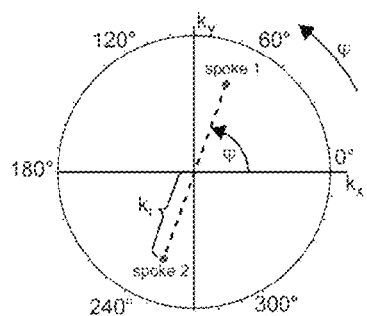
FIG. 6B
FIG. 6C
optimization: no $\Delta B_0$
simulation: with $\Delta B_0$
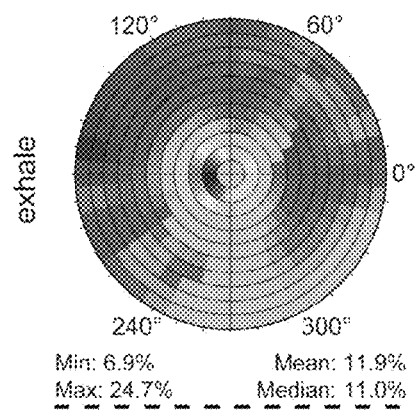
exhale
Min: 6.9%  Mean: 11.9%
Max: 24.7%  Median: 11.0%
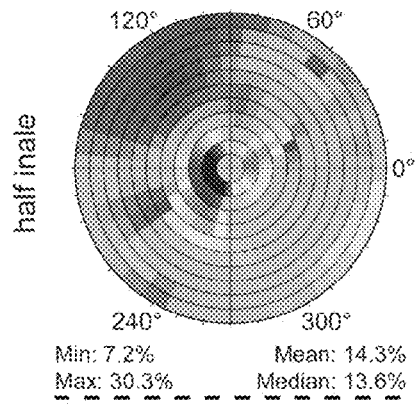
half inale
Min: 7.2%  Mean: 14.3%
Max: 30.3%  Median: 13.6%
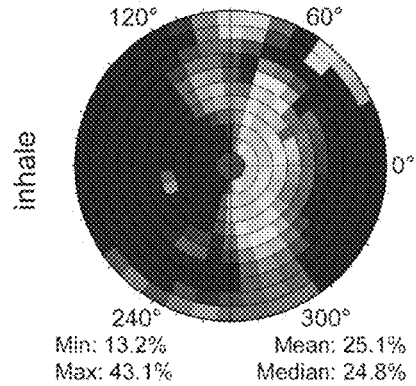
inhale
Min: 13.2%  Mean: 25.1%
Max: 43.1%  Median: 24.8%

SYSTEMS AND METHODS FOR DESIGNING MAGNETIC RESONANCE IMAGING RADIO FREQUENCY PULSES THAT ARE ROBUST AGAINST PHYSIOLOGICAL MOTION ERRORS

CROSS-REFERENCE TO RELATED APPLICATIONS

This application is based on, claims priority to, and incorporates herein by reference in its entirety, U.S. Provisional Application Ser. No. 61/984,268, filed Apr. 25, 2014, and entitled, "SYSTEMS AND METHODS FOR DESIGNING MAGNETIC RESONANCE IMAGING RADIO FREQUENCY PULSES THAT ARE ROBUST AGAINST PHYSIOLOGICAL MOTION ERRORS."

STATEMENT REGARDING FEDERALLY SPONSORED RESEARCH

This invention was made with government support under EB015894 awarded by National Institutes of Health. The government has certain rights in the invention.

BACKGROUND

The present disclosure relates to systems and methods for magnetic resonance imaging ("MRI"). More particularly, the disclosure relates to systems and methods for designing radio frequency ("RF") pulses for in-vivo MRI applications, where the RF pulses are robust against errors due to physiological motion of organs during the respiratory cycle.

Cardiac and respiratory motion causes the human heart to be among the most challenging organs for MRI. However, research has made significant progress recently to addressing those and other challenges allowing cardiovascular magnetic resonance (CMR) to become an indispensable tool among the different techniques to diagnose cardiovascular diseases.

Cardiac motion is typically addressed by acquiring the data in synchrony with the cardiac cycle, enabled by an electrocardiogram, pulse oximeter, or acoustic triggering devices. Respiratory motion is addressed in a variety of ways. A large fraction of acquisitions is acquired under single or multiple breath-holds, either performed during full inhalation, which is often more pleasant for the volunteers, or during expiration, which typically results in lower respiration variability between different breath-holds. The other fraction of cardiovascular acquisitions is performed during free-breathing, because of long scan times, patient compliance, or because breathing is deliberately wanted to identify a disease.

Most free-breathing protocols include navigator scans into the sequence, which monitor the respiration level based on the position of the diaphragm. Accordingly, only scans within a predefined acceptance window (typically around 7 mm wide) are included in the reconstructions. Within the acceptance window, the slice position is often prospectively corrected according to the diaphragm position with a fixed factor of typically 0.6. Navigator based acquisitions are relatively inefficient since only 30-50% of the acquisitions commonly fall within the acceptance window.

In order to reduce scan times, several recent studies have demonstrated that scan efficiencies of up to 100% are feasible while data is corrected retrospectively for respiratory motion. Furthermore, recent advances in hardware, pulse sequence design, and reconstruction algorithms have pushed acquisition speed towards real-time cardiac imaging enabling image acquisition times of less than 50 ms and during this period respiratory motion can be neglected.

In addition to the above-mentioned advances in cardiac MRI, there is also an ongoing trend towards higher fields. Despite challenges of banding artifacts, higher specific absorption rate (SAR) and contrast non-uniformities, an increasing number of clinical scans are performed at 3T.

MR scanners operating at a higher main magnetic field strength (B0) provide higher signal-to-noise ratio (SNR) and better acceleration performances in parallel imaging techniques, allowing for higher spatial resolution images and/or shorter acquisition times. Higher magnetic fields also provide stronger tissue contrast in a variety of applications.

Today, most clinical MR scanners operate at a B0 field of 1.5 Tesla (T) or 3 T, with 1.5 T typically considered standard field and 3T considered "high field." In recent years, a strong interest in systems operating at 7T, considered "ultra high field," or UHF, resulted in several tens of human 7T systems being installed in academic research centers, with a growing body of clinical research studies published every year at 7T.

Despite gains in SNR and tissue contrast, increased main magnetic field strengths are also faced with several challenges, including magnetic susceptibility induced B0 inhomogeneities and inhomogeneities of the transmit B1 field, or radiofrequency coils. These two issues are complicated by physiological motion that can alter $\Delta B_0$ and B1+ maps.

With respect to magnetic susceptibility induced artifacts, when a human body is placed in the homogeneous B0 field of an MR scanner, spatial perturbations of B0 ($\Delta B_0$) will occur, which are mainly induced by different magnetic susceptibilities between different biological tissues of the human body. In the presence of large $\Delta B_0$, severe artifacts of multiple kinds typically occur in the resulting images. Because $\Delta B_0$ variations are proportional to B0, larger artifacts occur as the field increases. So-called B0 Shimming coils help countering $\Delta B_0$ variations by applying additional magnetic fields trying to cancel undesired $\Delta B_0$ within a given region of interest. However, B0 shimming can only achieve partial correction this problem, and the magnitude of residual artifacts increases as the main magnetic field B0 increases. The $\Delta B_0$ also affects the spatial excitation profile of the RF pulses utilized to excite spins to generate the MR signals that are then sampled by the receiver chain.

The second challenge associated with increasing field strength is the shortened wavelength of the transmit RF field, due to the fact that MR operates at the Larmor frequency of protons which is proportional to B0. This can lead to significant variations of the transmit magnetic field (B1+) magnitude which consequently results in spatial variations of image intensity and image contrast. This problem is especially significant in the torso where the ratio of RF wavelength over organ size is even smaller, such as in the liver or in the heart. At clinical field strength of 3T B1+ variations of more than 50% over the heart have been reported. At 7T field strength, B1+ variations are intrinsically stronger, and can even cause a complete loss of B1+ in local area. The resulting contrast and signal intensity variations can significantly affect scientific results and deteriorate the diagnostic quality of the MR images.

Addressing spatial inhomogeneity of RF excitation to restore homogeneous tissue contrast can be achieved using a transmission RF coil including multiple, independent transmitting coil elements, knowing that the final excitation B1+ field is the superposition of the complex B1+ fields of each coil element. The simplest method, referred to a "B1+ shimming" includes applying a constant complex factor on each coil element scaling the amplitude and phase of the input RF power of each coil element. The complex factors are optimized to obtain a homogeneous superposition of the individual B1 fields.

A more powerful and general approach, referred to as "parallel transmission," or "pTX," additionally includes temporal changes, which means that at each time point (typically every 4 to 10 microseconds) of an RF pulse (with typical duration of 0.5 to 4 ms), the complex RF input on each individual channel can be varied independently to the others. A technique often referred to as "spokes," uses a series of sub-pulses (~0.5 ms/subpulse), each being plaid with a specific B1+ shim solution. This temporal flexibility, together with the use of gradient encoding moments, greatly increases the degrees of freedom, with higher excitation fidelity, to the cost of higher complexity and more expansive hardware than required for B1+ shim.

The calculation of the complex B1+ shimming factors or the pTX RF pulses is based on calibration scans, acquired prior to the respective imaging scan. These typically include spatial mapping of the B1+ field of each transmit element and potentially a $\Delta B_0$ map. The calculated RF pulses or B1+ shim factors are then applied for a dedicated sequence during the imaging scan.

A significant challenge is the possibility that the respiratory status of the patient/subject changes between the calibration scans (B1+ and B0 maps) and the actual imaging scan for which the B1+ shim solution or pTX RF pulse are applied. In practice, a good number of scans in the torso are acquired during breath-holds, where the patient is asked to always come back to a same exhale (or inhale) position; however, patients will not always return to the same position. This patient motion can significantly impact resulting image quality (e.g., with degradation of excitation homogeneity). This deleterious impact primarily comes from significant differences between the B1+ maps of individual RF coil elements (more so than differences in B0 maps) at different phases of the respiration cycle.

Accordingly, systems and methods are needed to manage these competing imaging constraints and sources of potential deterioration of the quality of the resulting clinical images.

SUMMARY

The present disclosure overcomes the aforementioned drawbacks by providing systems and methods for designing radio frequency ("RF") pulses for in-vivo MRI applications, where the RF pulses are robust against errors due to physiological motion of organs during the respiratory cycle. That is, two-spoke parallel transmission (pTX) RF pulses have been demonstrated in cardiac MRI at high fields, but the pulse designs rely on a single set of B1+/B0 maps that may not be valid for subsequent scans acquired at another phase of the respiration cycle, because of organs displacement. The present disclosure provides systems and methods for pTX RF pulse design that is robust against respiration induced variations of magnetic field maps. These robust RF pulse designs can be configured and/or optimized to perform over multiple B1 maps obtained in different physiological states, such as respiratory positions.

In accordance with one aspect of the disclosure, a magnetic resonance imaging (MRI) system is provided that includes a magnet system configured to generate a polarizing magnetic field about at least a region of interest (ROI) of a subject arranged in the MRI system, the ROI being subject to cyclical physiological motion including plurality of different states of physiological motion. The MRI system also includes a plurality of gradient coils configured to apply a gradient field with respect to the polarizing magnetic field and a radio frequency (RF) system configured to apply RF excitation fields to the subject and a acquire MR image data therefrom. The MRI system further includes a computer programmed to acquire a B1+ calibration map for each of a selected ones of the plurality of different states of physiological motion in the subject, wherein each B1+ calibration map is correlated with a state of the physiological motion in the subject during acquisition of the B1+ calibration map. The computer is further programmed to design an RF pulse waveform, using the B1+ calibration maps and correlated state of the physiological motion in the subject, that is robust against the physiological motion. The computer is also programmed to control the plurality of gradient coils and the RF system to produce an RF field based on the RF pulse waveform to acquire imaging data from the subject and reconstruct an image of the subject from the imaging data.

In accordance with another aspect of the disclosure, a method is provided for designing a radio frequency (RF) pulse for parallel transmission with a magnetic resonance imaging (MRI) system. The method includes determining a state of physiological motion including plurality of different states of physiological motion within a region of interest (ROI) of a subject without performing a navigator pulse sequence. The method also includes correlating a B1+ calibration map for each of a selected ones of the plurality of different states of physiological motion in the subject and assembling the B1+ calibration maps into groups of virtual slices within the ROI. The method further includes designing an RF pulse waveform for parallel transmission, using the B1+ calibration maps grouped into virtual slices and correlated state of the physiological motion in the subject, that is robust against the physiological motion by adjusting pulses in the RF pulse waveform relative to the groups of virtual slices to reduce errors in data acquired using the RF pulse waveform induced by the cyclical physiological motion in the ROI.

In accordance with yet another aspect of the disclosure, a method is provided for designing a radio frequency (RF) pulse for parallel transmission with a magnetic resonance imaging (MRI) system. The method includes providing a B0 calibration map for each of a plurality of different states of physiological motion in a subject and providing a B1+ calibration map for each of the plurality of different states of physiological motion in the subject. The method also includes optimizing an RF pulse waveform that is robust against physiological motion by designing the RF pulse waveform for specific states of physiological motion using the B0 and B1+ calibration maps provided for the specific states of physiological motion. The method further includes directing the MRI system to produce an RF field based on the optimized RF pulse waveform.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIG. 6B is a graphic illustration of spoke placement.

FIG. 6C is a series of polar plots created where ΔB0 was not included in the optimization, thus En and Emax are identical to the left column in FIG. 6A, but it is included for the Bloch simulation to calculate the nRMSE.

DETAILED DESCRIPTION

Figure 1:
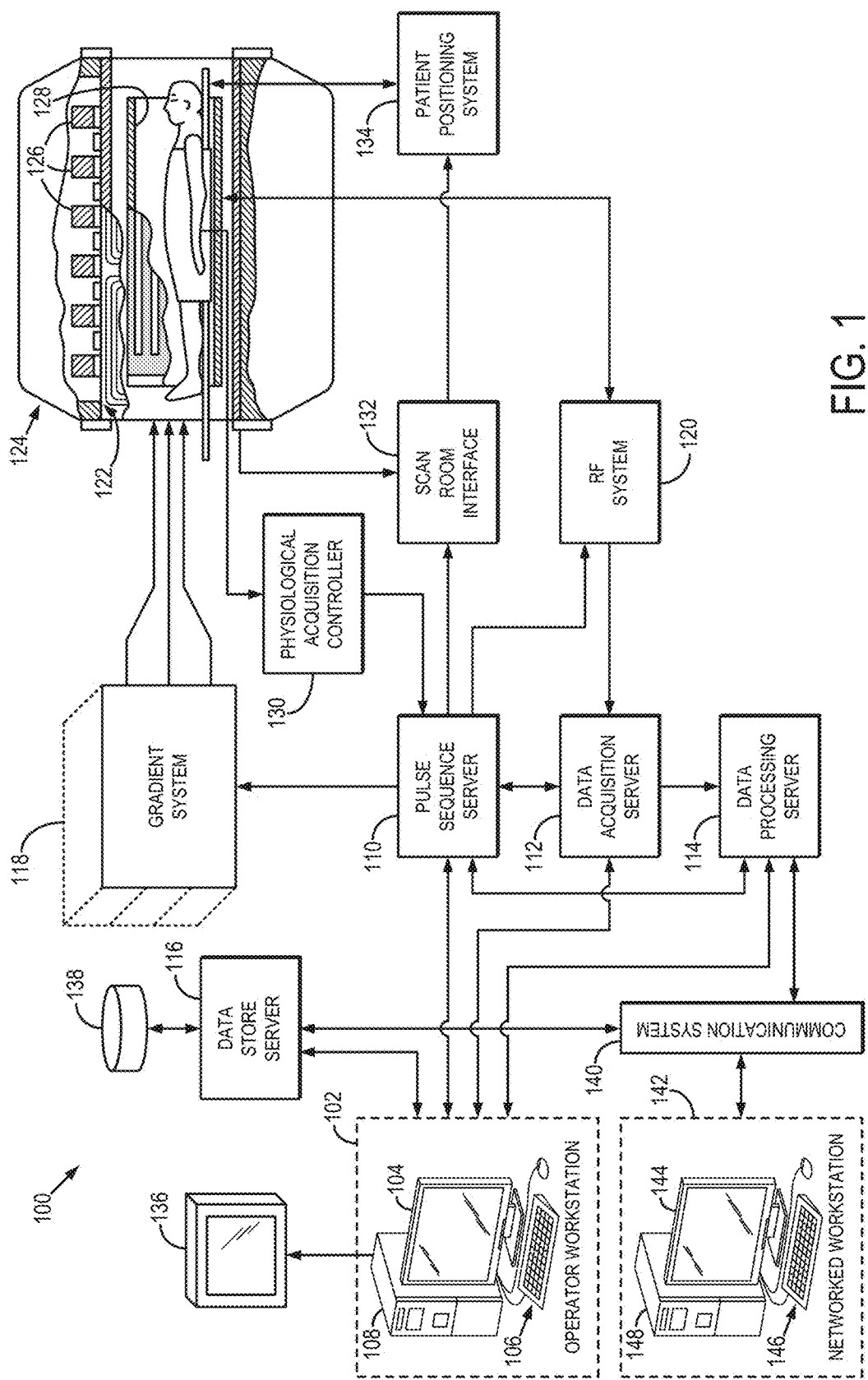
FIG. 1 is a block diagram of an example of a magnetic resonance imaging ("MRI") system.

Described here are systems and methods for designing radio frequency ("RF") pulses for in-vivo MRI applications, where the RF pulses are robust against errors due to physiological motion of organs for example caused by respiration. The existence of significant variations in B1+ maps and potentially B0 maps during the respiration cycle that have deleterious consequences on B1+ Shim and multi-channel RF Pulse design results is acknowledged. For example, RF pulses are designed based on multi-channel B1+ maps and potentially B0 maps acquired at different positions of the respiratory cycle (e.g., at least 2 points).

More generally, the systems and methods described here can be used to design RF pulses that are robust against errors arising from physiological motion by tailoring one or more RF pulses for a specific state of physiological motion. For instance, as noted above, an RF pulse can be designed specifically for a single position in a respiratory cycle. In some other embodiments, an RF pulse can be designed for a specific position associated with another state of physiological motion, such as a position in a cardiac cycle.

The systems and methods described here are also capable of designing RF pulses that are either specifically tailored for a single position in the respiratory cycle, or are tailored for multiple different positions in the respiratory cycle. For example, each position in the respiratory cycle can have a unique RF pulse associated with it. In another example, each position in the respiratory cycle can have the same RF pulse associated with it, wherein that RF pulse has been designed while taking into consideration all positions in the respiratory cycle. In still another example, a hybrid of these latter two approaches can be utilized. As one non-limiting example of a hybrid approach, if five positions are measured in the respiratory cycle, one RF pulse could be tailored for one position, another RF pulse tailored for another position, and a third RF pulse tailored to be robust against motion occurring across the remaining three positions.

By way of example, two different strategies to address the problems discussed above and to obtain solutions robust against respiratory changes within an imaging scan or between different scans are provided. Both methods utilize calibration scans (B1+ and potentially $\Delta B_0$ maps) performed at different respiratory positions (i.e., phase in the respiratory cycle). As an example, three positions can be sampled: exhalation, half-inhalation and inhalation. Each calibration scan is acquired together with a navigator scan capable of measuring the actual position of the diaphragm, which determines the phase in the respiratory cycle.

Thus, in some embodiments, B1+ shim or RF pulse solutions that are robust enough to be compatible with any of the calibrated respiratory position (e.g., simultaneous multi-position optimization) are designed. For instance, a B1+ shimming solution can be obtained, or a pTX RF pulse designed, based on simultaneously using the calibration scans obtained for the three positions of the respiratory cycle (inhale, half-inhale and exhale).

In some other embodiments, respiratory position is continuously sampled with navigator echoes measuring the diaphragm position in order to apply B1+ shim or RF pulses optimized for the particular measured position. For instance, an individual B1+ shim solution or pTX RF pulse can be calculated for each of the respiratory positions. Prior to the final imaging scan a fast navigator scan can be used to determine the current respiratory position and the B1+ shim solution or pTX RF pulse corresponding to this measured navigator position can then be applied for the subsequent acquisition.

The variations in $B_1^+$ (and $\Delta B_0$) can be attributable not only to the motion of internal organs during respiratory cycle, but also to deformations of those organs during the respiratory cycle. As one example, changes in the position of the heart during the respiratory cycle, changes in the shape of the heart during the respiratory cycle, or both, can result in variations in both $\Delta B_0$ and $B_1^+$. Changes in the position of the heart can be estimated as three-dimensional rigid motion, which may be further refined with local distortions to more accurately account for total heart motion plus deformation. Changes in the heart shape can be estimated as three-dimensional spatial deformations to the shape of the heart.

An example of a spoke pulse design that is informed by respiratory positions is now provided.

Single-spoke and multi-spoke RF pulses for cardiac CINE imaging can be designed in the small tip angle regime based on a spatial domain method using a magnitude least squares optimization:

$$\hat{b} = \arg\min \left( \||Ab| - |m|\|_w^2 + R(b) \right) \quad [1]$$

The fidelity term $\||Ab|-|m|\|_w^2$ denotes the quadratic deviation between the magnitude of the actual excitation pattern Ab and the target excitation pattern m (here m is constant throughout the region of interest). A is the concatenated system matrix including n=1 . . . N spatial points, k=1 . . . K transmit channels and s=1 . . . S spokes. Each element of the N×(K×S) matrix A can be expressed as:

$$a_{n,k+(s-1)\cdot K} = i\gamma m_0 \Delta T \cdot B_{l,k}^+(r_n) \cdot e^{i\gamma \Delta B_0(r_n)[t_s - T]} e^{2\pi i \cdot r_n \cdot k(t_s)}, \quad [2]$$

with $r_n$ the spatial coordinates, $B_{l,k}^+(r_n)$ the spatial transmit $B_1$ sensitivity profiles, $k(t_s)$ the spokes' k-space positions, $t_s$ the time at the center of each spoke RF pulse, T the total pulse duration, $\Delta T$ the duration between two sub-pulses, $\Delta B_0(r_n)$ the susceptibility induced deviations of the magnetic field $B_0$, $\gamma$ the proton gyromagnetic ratio and $m_0$ the equilibrium magnetization.

Accordingly, the vector b denotes the S×K complex weights for S spokes and K transmit elements (here S=2 and K=16). In this work, the regularization term R(b) in Eq. 1 is defined as $R(b) = \lambda^2 \|b\|^2$, which includes the total RF energy represented by $\|b\|^2$ weighted by a squared regularization parameter $\lambda$.

After RF pulse calculation, the flip angle (FA) map $\alpha(r)$, corresponding to the optimized result $\hat{b}$, is calculated using a Bloch simulation denoted by $f_{Bloch}$:

$$\alpha(r) = f_{Bloch}(\hat{b}, B_{l,k}^+, \Delta B_0) \quad [3]$$

The Bloch simulation typically matches well the actual experiments, assuming correct timing and gradient trajectory and assuming that $B_1^+$ and potentially $\Delta B_0$ did not change between the calibration scan and the actual imaging scan. The latter assumption, however, may be violated particularly in abdominal studies, because respiratory motion may alter spatial distributions of $B_1^+$ and $\Delta B_0$.

In the following, we consider P=3 different respiratory positions: end-exhalation (exhale), full inhalation (inhale) and half-inhale, with $\Delta B_0$ and $B_1^+$ calibration maps being experimentally measured in each position. In the following, we consider the situation where an RF pulse, designed based on calibration maps acquired at position $p_{reference}$, is actually applied during a scan at $p_{actual}$. The resulting excitation pattern becomes:

$$\alpha(r)|_{p_{actual}}^{p_{reference}} = f_{Bloch}(\hat{b}|_{p_{reference}}, B_{l,k}^+|_{p_{actual}}, \Delta B_0|_{p_{actual}}) \quad [4]$$

For clarity, throughout the examples provided below, the position $p_{reference}$ for the conventional RF pulse design is taken to be exhalation and the superscript is neglected ($p_{reference}$=exhale). To investigate the impact of respiration, the corresponding flip angles for three different positions $p_{actual}$ can be simulated to obtain $$\alpha(r)|_{exhale}^{exhale}, \alpha(r)|_{half-inhale}^{exhale} \text{ and } \alpha(r)|_{inhale}^{exhale}.$$

In order to achieve an RF pulse that is robust against respiratory changes, the optimization can be expanded to cover multiple respiratory positions. Assuming the calibration maps from $\tilde{P}$ different positions are selected out of the P total acquired calibration positions, then the optimization can be performed simultaneously for all $\tilde{P}$ positions by expanding matrix A (see equation 1) along the spatial dimension. This concept is equivalent to treating the different positions as virtual slices (i.e. with slice distance 0), and each virtual slice may have different target regions-of-interest ("ROIs") $w_i$ and different target magnetizations $m_i$:

$$A_{virtual} = \begin{bmatrix} A_1 \\ A_2 \\ \vdots \\ A_{\tilde{P}} \end{bmatrix}, m_{virtual} = \begin{bmatrix} m_1 \\ m_2 \\ \vdots \\ m_{\tilde{P}} \end{bmatrix}, w_{virtual} = w_1 \cup w_2 \ldots \cup w_{\tilde{P}}. \quad [5]$$

In this example, the magnitude of m is set to 1 for all positions and the $\tilde{P}$ ROIs $w_1 \ldots w_{\tilde{P}}$ are defined for the different calibration datasets used for RF pulse design. The final optimized result is then obtained by solving the following minimization problem:

$$\hat{b}_{virtual} = \arg\min(\||A_{virtual}\cdot b| - |m_{virtual}|\|_{w_{virtual}}^2 + R(b)). \quad [6]$$

The flip angle map expected for the respiration state $p_{actual}$ is then given by $a(r)|_{p_{actual}}^{Preference}$ with $p_{reference}$ representing the combined $\tilde{P}$ virtual slice positions. A robust RF pulse design can be achieved by performing a simultaneous optimization on $\tilde{P}=2$ positions (exhale and inhale) while resulting FA maps can be simulated at a larger number of positions, for example P=3: $a(r)|_{exhale}^{(exhale,inhale)}$, $a(r)|_{half-inhale}^{(exhale,inhale)}$ and $a(r)|_{inhale}^{(exhale,inhale)}$ Referring particularly now to FIG. 1, an example of a magnetic resonance imaging ("MRI") system 100 is illustrated. The MRI system 100 includes an operator workstation 102, which will typically include a display 104; one or more input devices 106, such as a keyboard and mouse; and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (7);$$

and the phase of the received magnetic resonance signal may also be determined according to the following relationship:

$$\varphi = \tan^{-1}\left(\frac{Q}{I}\right). \qquad (8)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Provided hereafter are several non-limiting examples of particular implementations of systems and methods consistent with the present disclosure.

Example 1: pTX RF Pulse Design Robust Against Respiration in Cardiac MRI at 7T System and Setup In this example, experiments were performed on a whole body 7T magnet equipped with a prototype 16-channel pTX system. A 16-channel transmit/receive body coil was used having 8 posterior elements positioned under the subject's back and 8 anterior coil elements positioned on the chest. Four subjects were scanned, who signed a consent form approved by a local Institutional Review Board. The cardiac cycle was recorded using an electrocardiogram (ECG) with three leads attached to the subject's chest. Due to the magneto-hydrodynamic effect, the detection of the cardiac cycle using an ECG is challenging at 7T; therefore, the electrodes were repositioned if the cardiac trigger was erroneous. Scans were acquired in all four subjects in three different orientations: transversal, short axis and pseudo four-chamber view. Post-processing of the calibration scans, RF pulse design and Bloch simulations were performed offline using Matlab (The Mathworks, Nattick, Mass., USA).

Respiratory Controlled Calibration Scans

Above, P=3 different respiratory positions were described unless otherwise noted: exhale; half inhale and inhale. In one of the subjects in this example, P=4 different positions were investigated between end-expiration and end-inhalation, that were treated analogous to the P=3 scans. For each of these positions calibration datasets including $B_1^+$ sensitivity profile mapping of the K=16 TX channels and spatial maps of $\Delta B_0$ were acquired. These scans were performed during one breath-hold in a single slice of the heart in each orientation.

$B_1^+$ maps were obtained using a modified fast $B_1^+$ estimation technique. The method used acquires 16 cardiac triggered small flip angle gradient echo (GRE) images for which only a single TX channel is active per image while all channels are enabled for reception. Parameters for this scan were chosen as follows:

TE=2.6 ms/TR=4.7 ms,
Bandwidth=801 Hz/Pixel,
Matrix=160×104, and
Resolution=2.8×2.8×5 mm.

Each GRE image was acquired in a FLASH-like approach during diastole of a single heartbeat which allowed for a total acquisition time of less than 20 s, which was a feasible breath-hold duration for all subjects. The short acquisition duration of 436 ms allowed for a second image acquired during the same heartbeat prior to each GRE image in sagittal view covering the diaphragm dome (see FIG. 2a). As a result, the diaphragm position was recorded 16 times, which allowed retrospective verification of the diaphragm position and identify potential changes in the respiratory position throughout the $B_1^+$ mapping process.

$B_0$ mapping was performed in a similar way for each respiratory position and each orientation using an ECG triggered dual-TE GRE acquisition performed under breath-hold. Either of the two phase images was acquired during a single cardiac cycle together with an image of the diaphragm obtained at the same sagittal location as for $B_1^+$ mapping. TE was alternated between subsequent heartbeats and $B_0$ maps were averaged over 4 acquisitions. The following parameters were used:

TE1=3.1 ms/TE2=4.1 ms/TR=4.7 ms,
Bandwidth=919 Hz/Pixel,
Matrix=160×104,
Resolution=2.8×2.8×5 mm A third scan was performed targeting only the diaphragm. During this non-triggered acquisition the subject was asked to slowly but deeply breath in and out for several breathing cycles. The following parameters were used:

TE=2.3 ms/TR=4.1 s,
Bandwidth=1488 Hz/Pixel,
Matrix=160×160,
Resolution=2.8×2.8×5 mm.

The objective for this scan was to acquire images of the diaphragm at different respiratory phases of the breathing cycle covering the entire spectrum from end-exhalation to end-inspiration. This scan was used as a reference to identify and verify the respiratory positions.

RF Pulse Design and RF Pulse Performance

Single-spoke and 2-spoke RF pulses were designed using the conventional RF pulse design based on exhale calibration maps and using an energy based regularization parameter as defined above. Therefore, for each orientation three ROIs denoted by $w_{exhale}$, $w_{half-inhale}$ and $w_{inhale}$ were manually generated based on the $B_1^+$ calibration data, covering the heart in each respiratory position. The two spokes were placed symmetrically with respect to $k_x=k_y=0$ and played out along the $k_z$ axis. The "spokes axis," which is defined by the connecting line from spoke 1 to spoke 2 (compare dashed line in FIG. 6b), was rotated by an angle varying from 00 to 360° in 10° steps, while the spoke radius, $$k_r = \left|\frac{\gamma}{2\pi}\int G dt\right|,$$

varied from 0 to 10 m$^{-1}$ in steps of 1 m$^{-1}$. Each RF pulse design was performed for the resulting 361 different 2-spoke trajectories using two 800 μs long, SINC shaped RF sub-pulses with bandwidth-time-product (BWTP) of 4 in combination with a slice selection gradient achieving 5 mm slice thickness. The 1-spoke RF pulses were played out along k$_z$ at k$_x$=k$_y$=0 an the optimization was performed 361 times using different starting phase pattern for the target vector m, thus yielding the same number of solutions as for 2-spokes. The same SINC shaped RF pulse with BWTP=4 was used as the 2-spoke sub-pulse, but the duration was stretched to 1600 μs to maintain the same total duration.

In addition to the conventional RF pulse design, the robust RF pulse design was applied for the 2-spoke RF pulses and demonstrated in-vivo. Here, the RF pulse design was based on both the exhale and the inhale respiratory position, while the RF pulse duration, shape and BWTP were unchanged compared to the conventional RF pulse design.

For each solution the normalized energy E$_n$ (20,25) was calculated by normalizing the total pulse energy ‖b‖$^2$ by the square of the average value of the FA over the ROI of the reference calibration, denoted by mean |Ab|$_{W_{reference}}$. The maximum energy per channel E$_{max}$=max(E$_k$), was calculated for each solution. FA maps $a(r)|_{P_{actual}}^{P_{reference}}$ were generated with Bloch simulations (see Eq. 4) for a target FA of α$_1$=10°, for the 361 solutions obtained at each respiratory position for the conventional pulses as well as for the robust pulses. For each map the normalized root-mean-square error was calculated as follows:

$$nRMSE|_{P_{actual}}^{Preference} = \frac{1}{N_{P_{actual}} \cdot a_t}\sqrt{\sum_{n \in w_{P_{actual}}}(a_t - a(r_n)|_{P_{actual}}^{Preference})^2}. \quad [9]$$

Here, N$_{P_{actual}}$ denote the number or voxels in ROIs w$_{P_{actual}}$. The RF pulse amplitude was normalized such that the average FA for the reference position, i.e. $a(r)|_{exhale}^{exhale}$ for the standard pulse design, as well as $a(r)|_{exhale}^{(exhale,inhale)}$ and $a(r)|_{inhale}^{(exhale,inhale)}$ for the robust design, matches the target FA of 10°. Note that, in the inhale Results section, nRMSE will be expressed in percent.

In situations when high RF power levels are utilized to achieve small nRMSE|$_{exhale}^{exhale}$ values, small changes of a few percent are of significantly higher importance compared to excitations with larger nRMSE|$_{exhale}^{exhale}$ values. Therefore, relative changes in nRMSE were also calculated for the conventional RF pulses:

$$R_{exhale}^{half-inhale} = \frac{nRMSE|_{half-inhale}^{exhale}}{nRMSE|_{exhale}^{exhale}}, \quad R_{exhale}^{inhale} = \frac{nRMSE|_{inhale}^{exhale}}{nRMSE|_{exhale}^{exhale}}. \quad [10]$$

For the 2-spoke pulses, nRMSE, E$_n$ and E$_{max}$ are displayed in polar coordinates as a function of the spoke radius k$_r$ and the spoke angle φ.

SAR Calculation

Electromagnetic (EM) simulations of the 16 channel transceiver coil loaded with a body model at exhale respiratory position were performed using a finite difference time domain solver (such as available from Remcom, Pittsburgh, Pa.). Based on the resulting EM fields, the same conventional RF pulse optimization was performed as for the in-vivo CINE acquisition, as described below, and global and local 10 g average SAR were calculated using identical sequence parameters. The lack of body EM models for other respiratory positions made it impossible to perform numerical simulations (including SAR) using the respiration robust RF pulse design. Therefore, to ensure safe in-vivo operation in compliance with the IEC guidelines, all experiments were obtained within conservative SAR limits: 10 g local SAR values, calculated according to the RF pulses effectively applied, amounted to 4 W/kg (global SAR: 0.33 W/kg), thus providing a safety factor of 10 towards the short term 10 g average local SAR first level limit. Furthermore, each CINE acquisition (with a maximum duration of 30 s each) was only applied at intervals of ≥3 minutes, corresponding to 6 minute averaged 10 g local SAR values of 0.67 W/kg providing a safety margin of a factor 30 compared to the 6 minute first level IEC guideline limit of 20 W/kg. These same conservative settings were applied to perform the CINE in-vivo scan, using an RF excitation pulse obtained with the robust RF pulse design, which was chosen to have similar energy (102%) as the conventional RF pulse. In this study, the configuration of our pTX system imposed a same absolute upper limit in RF power for each of the 16 channels; therefore the RF energy was identically limited for each channel (rather than considering the maximum sum of RF energy through the 16 channels).

CINE Acquisition

A comparison of the conventional and the robust RF pulse design is performed in-vivo using 2-spoke RF pulses with an ECG triggered CINE acquisition in transverse view. This acquisition is performed for both RF pulse designs with breath-hold positions exhale, half-inhale and inhale, respectively. CINE acquisitions were performed using the following parameters:
TE=2.6 ms/TR=44.8 ms/echo-spacing=5.6 ms,
8 segments,
25 cardiac phases,
Bandwidth=554 Hz/Pixel,
Matrix=192×124,
Resolution=2.3×2.3×5 mm,
GRAPPA=2.

Results

Impact of Respiration on Conventional Spoke RF Pulse Design

Figure 2A:
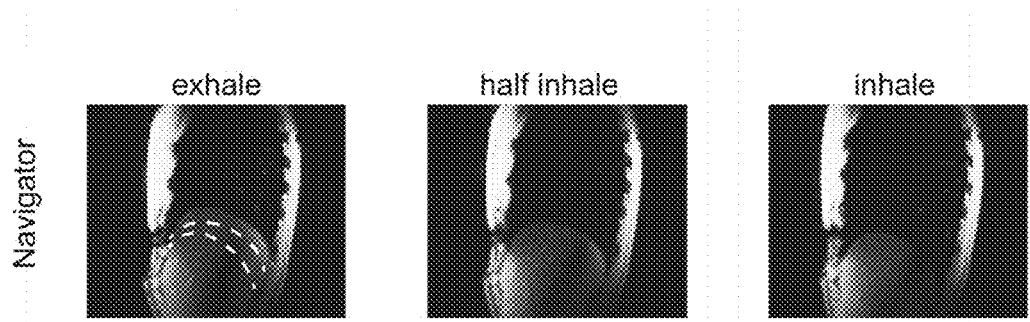
FIG. 2A is a series of navigator images acquired for three different respiratory positions, where the dashed lines in the leftmost image indicate the respective diaphragm position in the two other respiratory states.
Figure 2B:
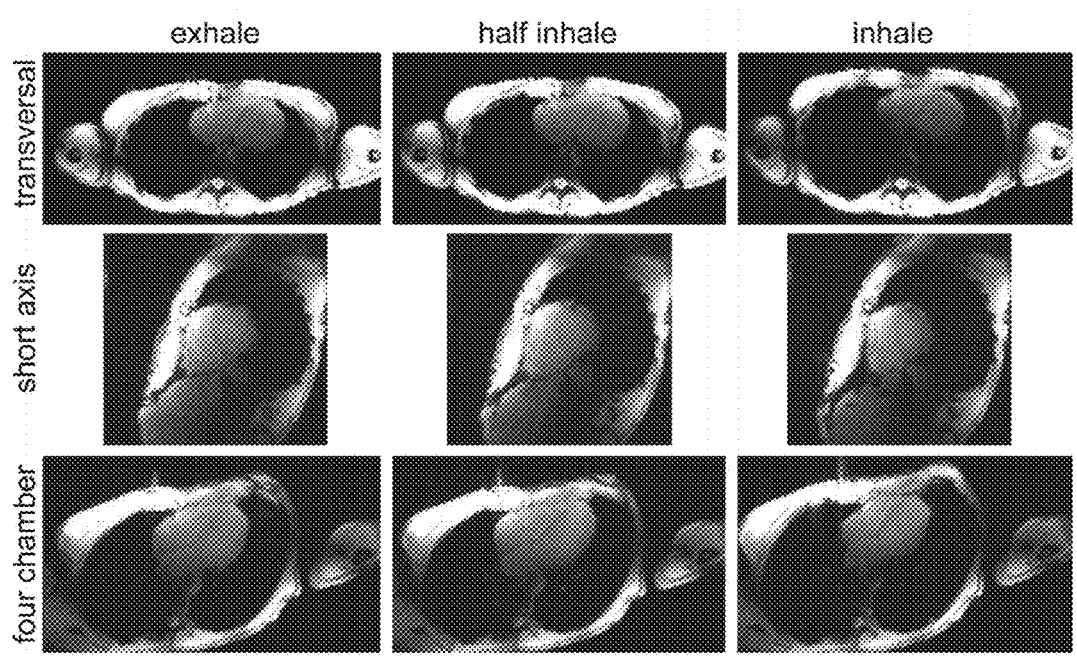
FIG. 2B is a set of magnitude images obtained from B0 acquisitions in the same respiratory positions corresponding to FIG. 2A for transversal, short axis and four chamber view.

FIG. 2a illustrates three navigator images of the diaphragm at different respiratory positions (exhale, half inhale and inhale). For each of the positions, FIG. 2b shows the magnitude images of the B$_0$ calibration scans acquired for each of the three respiratory positions in transversal, short axis and pseudo four chamber view. All images were acquired with a static B$_1^+$ phase shim setting that optimizes the resulting |B$_1^+$| homogeneity for the exhale position in transverse view. Therefore, areas of low |B$_1^+$| can be depicted in the navigator images as well as in the short axis and four chamber view images. Moreover, the transverse images illustrate a reduction of contrast homogeneity with increasing respiration (see arrow), which indicates alterations of $B_1^+$ and/or $B_0$ with different respiratory positions.

Figure 3A:
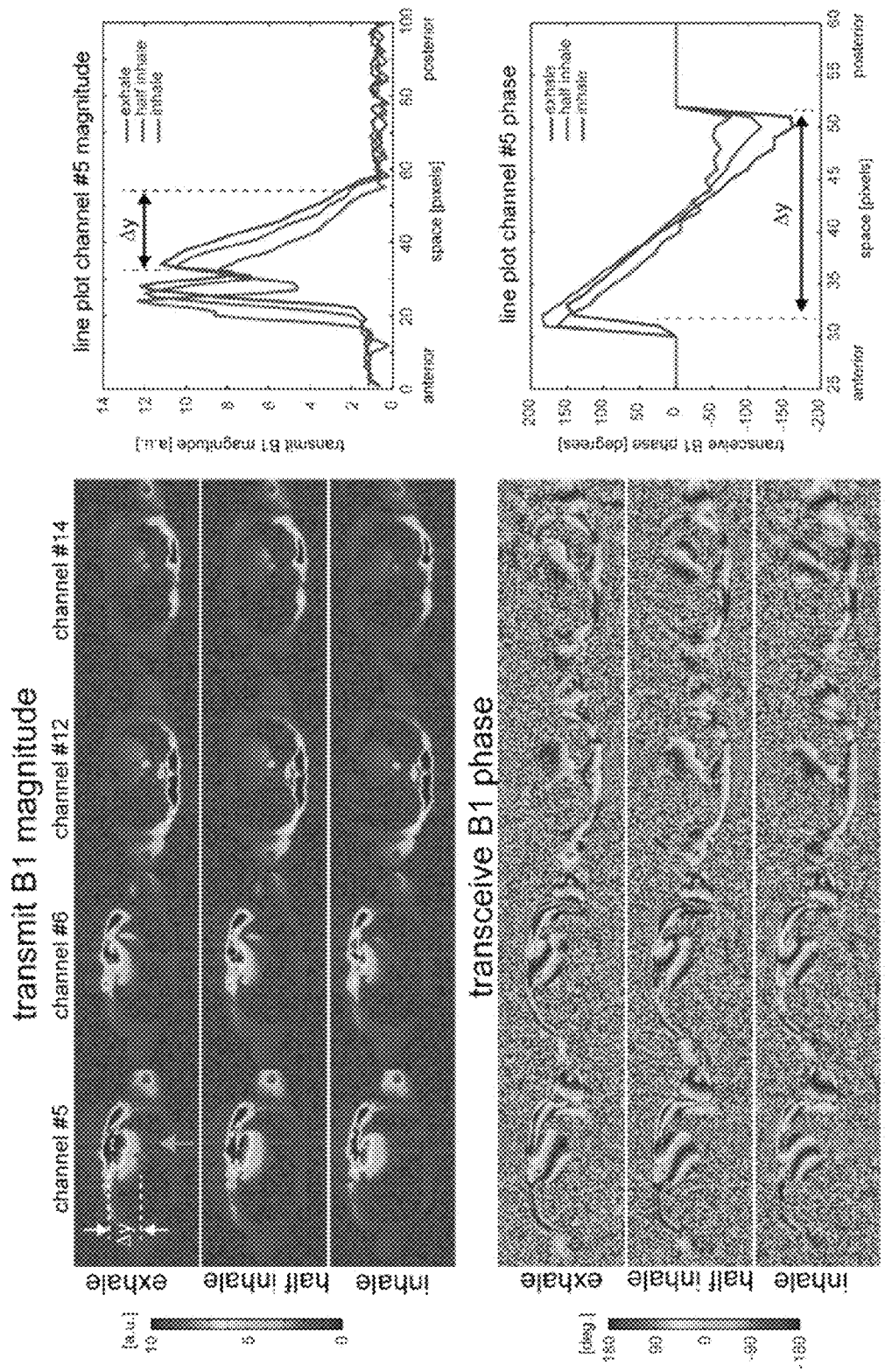
FIG. 3A is a report showing magnitude B1+ profiles and transceive phase profiles of the two most contributing anterior and posterior coil elements, accompanied by diagrams showing line plots along the vertical dashed line.
Figure 3B:
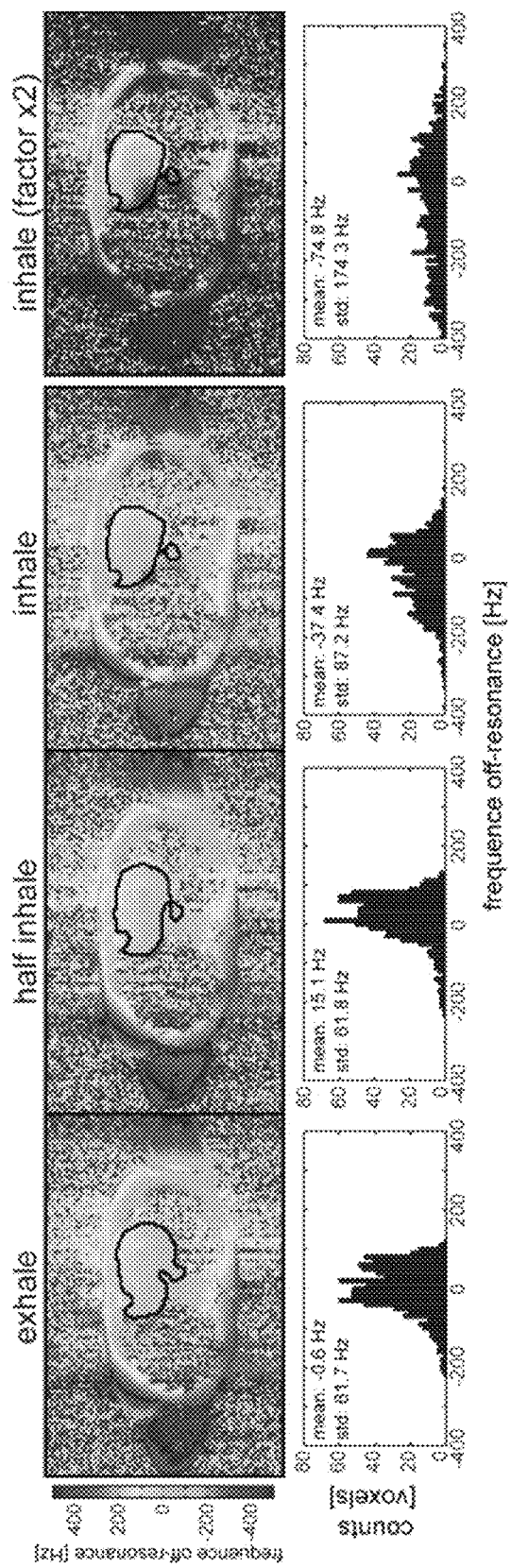
FIG. 3B is a report showing ΔB0 variations for three different respiratory positions and corresponding histograms of the ΔB0 distribution within the respective ROIs, where the rightmost diagrams show ΔB0 maps for the inhale respiratory position, multiplied by a factor of 2.
Figure 4A:
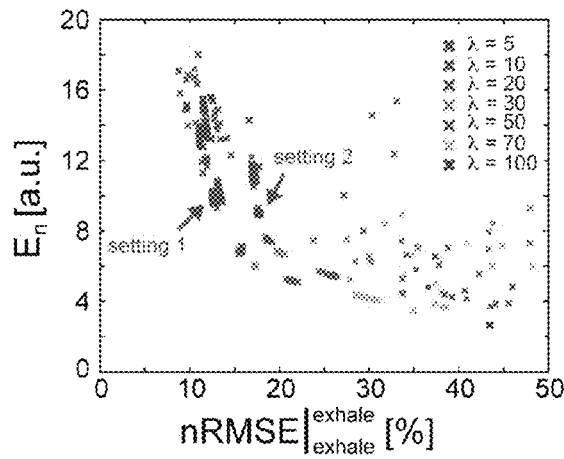
FIG. 4A is graph showing 1-spoke optimization curve between Energy (En) and nRMSE in exhale position for different tradeoff parameters λ. The diagram reveals two different L-curves, among which the curve closer to the origin describes acceptable solutions whereas the upwards shifted curve reflects solutions with a pronounced |B1+| minimum within the ROI.
Figure 4B:
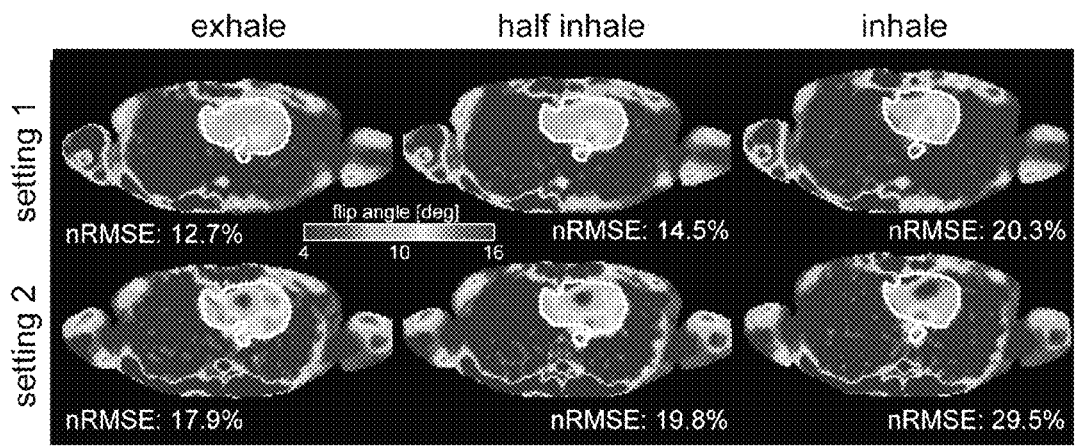
FIG. 4B is a set of reports for two examples (setting I and II marked in FIG. 4A) for three different respiratory positions.
Figure 4C:
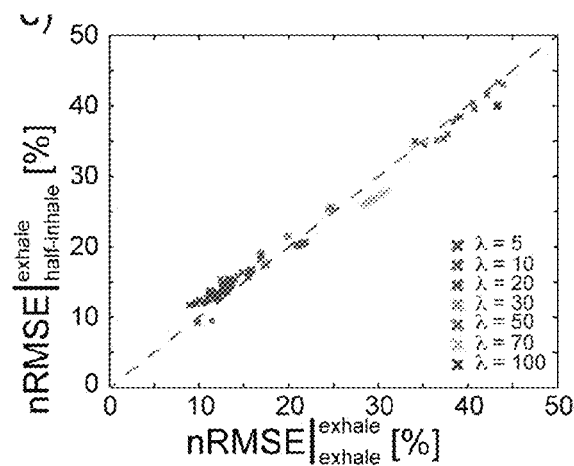
FIG. 4C is a graph showing changes of nRMSE with different breathing positions for nRMSE (half inhale) as a function of nRMSE(exhale) for different λ values.
Figure 4D:
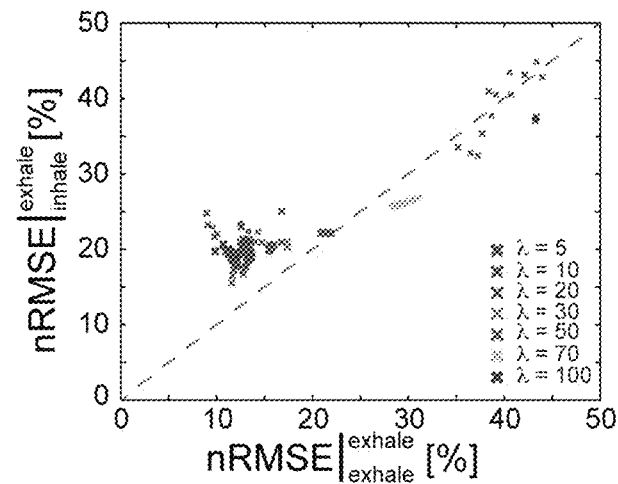
FIG. 4D is a graph showing changes of nRMSE with different breathing positions for nRMSE (inhale) as a function of nRMSE(exhale) for different λ values.
Figure 4E:
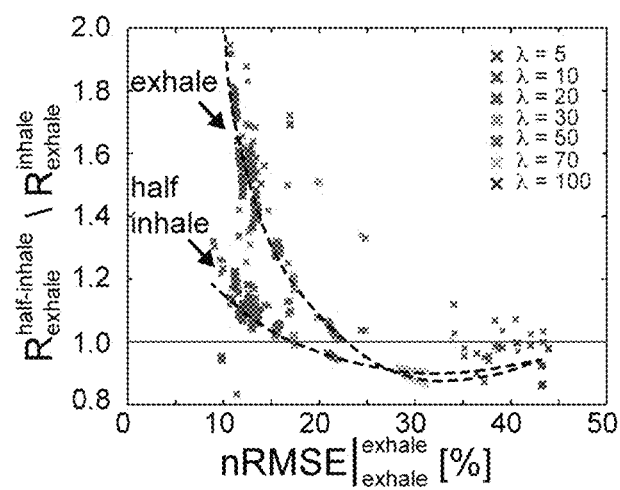
FIG. 4E is a graph showing relative changes of the diagrams shown in FIGS. 4C and 4D as ratio values for the half inhale and inhale position.

Changes of the $B_1^+$ magnitude with increasing respiratory volume are illustrated in FIG. 3a for the two most contributing anterior and posterior coil elements, respectively. Although the individual $B_1^+$ maps for the different respiratory positions appear to be similar, line plots through the heart along the dashed line in channel 5 (right plot in FIG. 3a) reveal a shift of the profile towards anterior resulting in a $|B_1^+|$ reduction of up to 30% between expiration and inhalation at a given location y. Similar changes can be observed in the $\Delta B_0$ corrected transceiver phase pattern, illustrated in FIG. 3b. The spatial transceiver phase profile also vary with respiration, as shown in FIG. 3b (note that $\Delta B_0$ induced phase variations have been subtracted from these plots), and the corresponding line plots reveal transceiver phase changes of 33° between exhale and half inhale and 55° between exhale and inhale as measured in the anterior part of the heart. Maps of $\Delta B_0$ and histograms of corresponding values within the ROI, shown in FIG. 3c, illustrate measured variations of $\Delta B_0$ with respiratory position. Although the mean $\Delta B_0$ value changes only moderately by ~37 Hz between exhale and inhale, local $\Delta B_0$ (see arrow) can reach up to more than 100 Hz, which is also reflected in an increase of the standard deviation from 62 Hz to 87 Hz.

FIG. 4 summarizes the impact of respiration-induced $\Delta B_0$ and $B_1^+$ alterations on 1-spoke RF pulses that were designed based on the respiratory exhale position. The tradeoff curve between $E_n$ and $\text{nRMSE}|_{exhale}^{exhale}$ for the 1-spoke RF pulses optimization is shown for different regularization parameters $\lambda$ in FIG. 4a, reflecting the traditional L-curved behavior. The optimization, which utilized 361 different starting phase sets for each $\lambda$ value, tends to result in two set of solutions, forming two separate L-curves. As illustrated exemplarity in FIG. 4b for $\lambda=10$ (see arrows in FIG. 4a), one set achieves a homogeneous excitation pattern whereas the second set provides less optimal solutions showing a local $B_1^+$ minimum within the ROI. Thus, only the first set of solutions was considered for all subsequent analysis. As specified in exhale FIG. 4b (top) the $\text{nRMSE}|_{exhale}^{exhale}$ value of 12.7% degrades towards values of 14.5% for $\text{nRMSE}|_{half-inhale}^{exhale}$ and 20.3% for $\text{nRMSE}|_{inhale}^{exhale}$. This trend is investigated in more detail for all $\lambda$ values in FIG. 4c+d, which displays $\text{nRMSE}|_{half-inhale}^{exhale}$ and $\text{nRMSE}|_{inhale}^{exhale}$ as a function of the $\text{nRMSE}|_{exhale}^{exhale}$. The diagrams reflect that using lower $\lambda$ values to achieve better excitation fidelity tends to increase the sensitivity towards respiration induced excitation profile imperfections, particularly for the inhale position. This trend becomes more apparent in FIG. 4e, which reflects the same data but displays the y-axis in relative values $R_{exhale}^{half-inhale}$ and $R_{exhale}^{inhale}$ (see equation 8). For $\lambda=5$, the nRMSE value can increase by a factors between 1.4 and 1.9, depending on the initial phase setting used for the optimization.

Figure 5A:
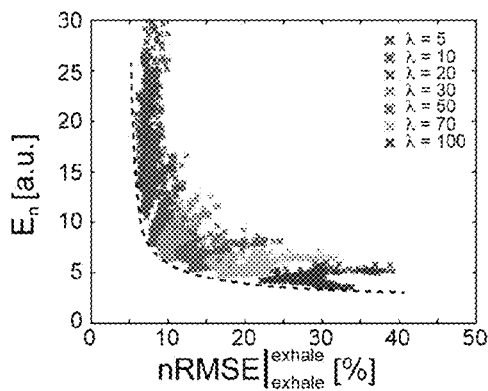
FIG. 5A is a graph showing 2-spoke optimization curve between Energy (En) and nRMSE in exhale position optimized for 361 different spoke trajectories and seven different tradeoff parameters λ.
Figure 5B:
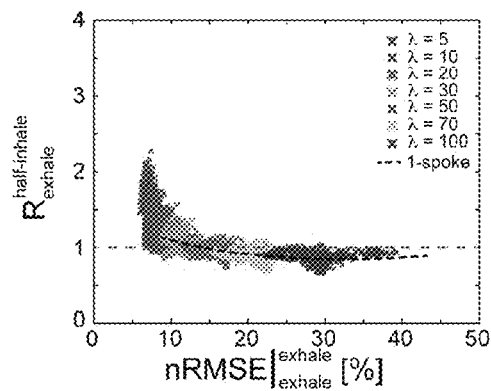
FIG. 5B is a graph showing relative changes of nRMSE expressed as ratio values for half inhale as a function of nRMSE (exhale).
Figure 5C:
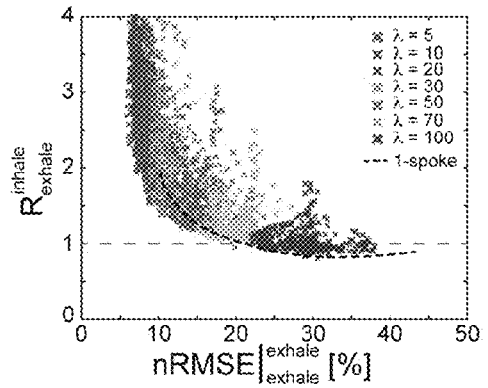
FIG. 5C is a graph showing relative changes of nRMSE expressed as ratio values for inhale as a function of nRMSE (exhale).
Figure 5D:
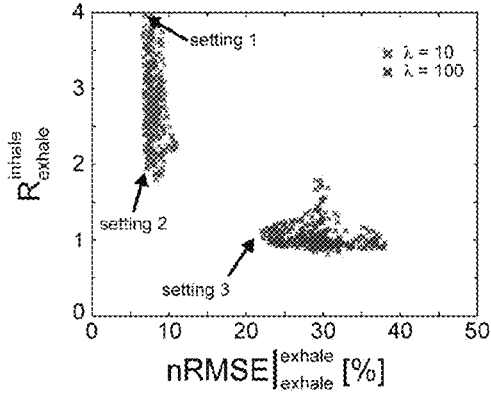
FIG. 5D is a graph showing the same results as in FIG. 5C highlighting the spread of the 361 solutions for a low and a high tradeoff parameter value (λ=10 and λ=100).
Figure 5E:
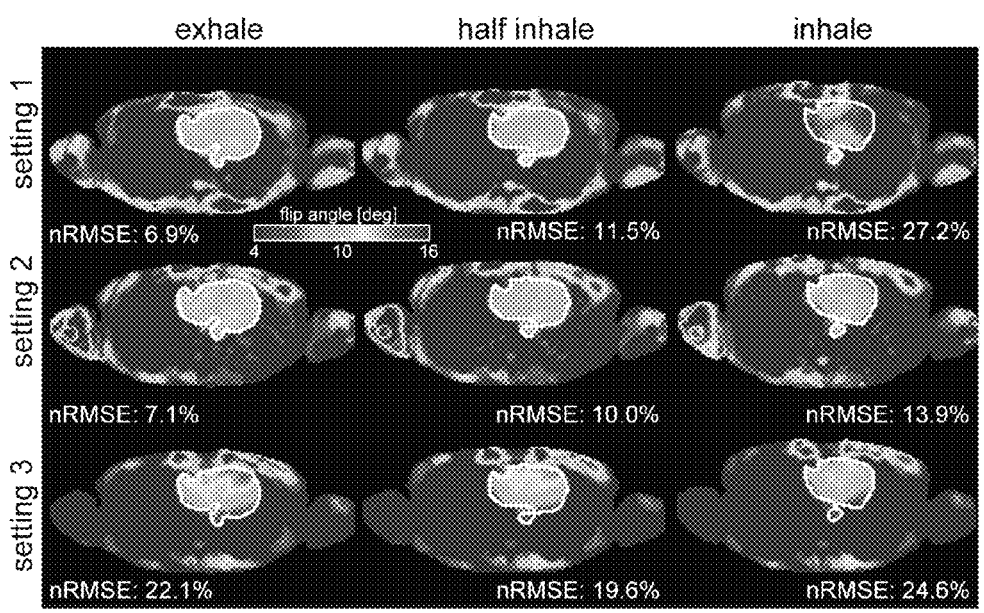
FIG. 5E is a set of reports for Bloch simulations of three different solutions, marked FIG. 5D for the different respiratory positions.

FIG. 5a shows the tradeoff between $E_n$ and $\text{nRMSE}|_{exhale}^{exhale}$ for the 2-spoke optimization. Each cross denotes a single optimization for a given $\lambda$ value and for one out of 361 different 2-spoke trajectories. In comparison to 1-spoke excitations shown in FIG. 4a, a reduction of $\text{nRMSE}|_{exhale}^{exhale}$ can be achieved for the same energy level with 2 spokes. For example using the same energy as the 1-spoke solution shown in FIG. 4a (top, left) the $\text{nRMSE}|_{exhale}^{exhale}$ value of 12.7% can be reduced to 7.2% by using a 2-spokes design (data not shown). This finding is in agreement with previous results (1). The impact of respiration on the different exhale optimized 2-spoke solutions is visualized in FIG. 5b+c by plotting $R_{exhale}^{half-inhale}$ and $R_{exhale}^{inhale}$ as a function of $\text{nRMSE}|_{exhale}^{exhale}$. The diagrams reflect the same trend as seen for 1-spokes results, the latter are visualized by dashed curves that are copied from FIG. 4e. 2-spokes RF pulses with small $\lambda$ values ($\lambda<20$) can achieve lower $\text{nRMSE}|_{exhale}^{exhale}$ values compared to 1-spokes, but these solutions are more sensitive towards respiration characterized by high $R_{exhale}^{half-inhale}$ and $R_{exhale}^{inhale}$ values. Furthermore, the scatter of $R_{exhale}^{inhale}$ values increases with decreasing $\lambda$ value and the scatter of nRMSE decreases with decreasing $\lambda$ values as demonstrated in FIG. 5d for $\lambda=10$ ($\text{nRMSE}|_{exhale}^{exhale}$ interval: 6.7%-10.9%; $R_{exhale}^{inhale}$ interval: 1.8-4.7) and $\lambda=100$ ($\text{nRMSE}|_{exhale}^{exhale}$ interval: 22.1%-39.0%; $R_{exhale}^{inhale}$ interval: 0.8-1.8). The impact on the excitation is visualized in FIG. 5e for three different settings that are marked in FIG. 5d. The solution shown in the first row is highly susceptible to respiration ($R_{exhale}^{half-inhale}=1.7$, $R_{exhale}^{inhale}=3.9$) with an $\text{nRMSE}|_{exhale}^{exhale}$ value of 27.2% and a corresponding flip of 7.4°. In contrast, the second setting having a similar $\text{nRMSE}|_{exhale}^{exhale}$ value of 7.1% is more robust towards respiration showing an $\text{nRMSE}|_{inhale}^{exhale}$ of 13.9% with a mean flip angle of 9.3°. The shape of the excitation profile for setting 3 ($\lambda=100$) is dominated by the coil's transmit sensitivity profiles characterized by a posterior-anterior slope in the flip angle. This results in a higher $\text{nRMSE}|_{exhale}^{exhale}$ value of 22.1%, which, however, changes by only 2.5% with respiratory positions.

Analysis of 2-Spoke Pulses in Polar Coordinates

Figure 6A:
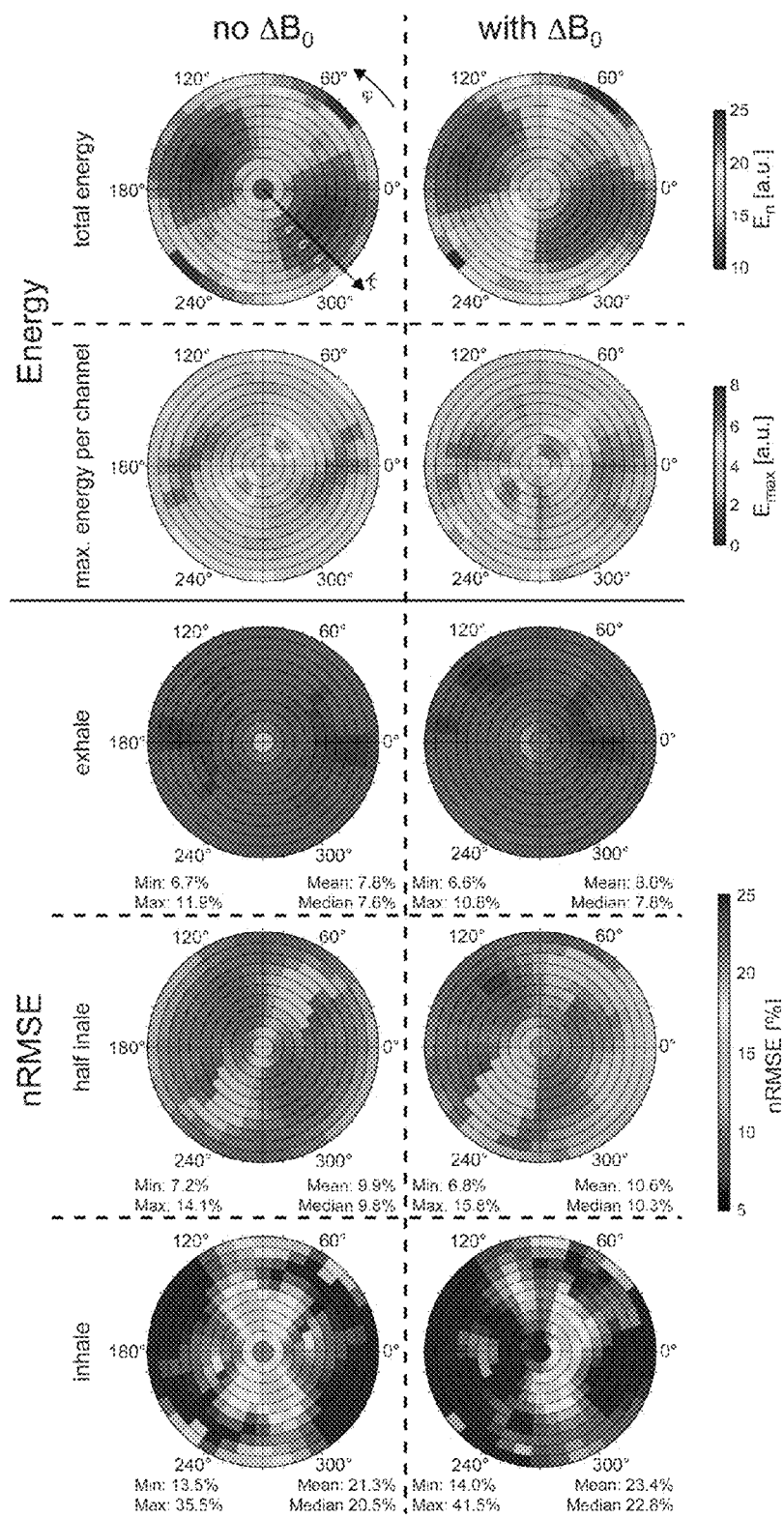
FIG. 6A is a series of polar plots of En, Emax and nRMSE values as a function of the 2-spoke k-space trajectories defined by the radius kr and the phase φ of the spokes axis illustrated in FIG. 6B. In the left column, ΔB0 is neither included in the pulse optimization nor in the Bloch simulations, which are used for the nRMSE calculation. In the right column, ΔB0 is included in both, the optimization and the Bloch simulation.

FIG. 6a investigates $E_n$, $E_{max}$ and nRMSE as a function of the two spokes locations given in polar k-space coordinates $k_r$ and $\varphi$ (see FIG. 6b). Optimizations and energy calculations were performed based on calibration maps obtained in exhale position while nRMSE values were calculated from Bloch simulations based on calibration maps of each respective respiratory position. Significant variation of $E_n$, $E_{max}$ and nRMSE is observed as a function of the spoke placement; corresponding maximum, minimum, mean and median values are listed below each polar plot. The results in the left column, which were obtained with $\Delta B_0$ set to 0 for optimization and simulation, show a 180° rotational symmetry. For this case the optimization is independent of the RF timing, thus, a permutation of the spokes in k-space achieves the same result (compare equation 2). In order to compensate the coil's $B_1^+$ variations along the anterior-posterior direction, optimal spoke placements are located along the 0°-180° exhale axis as seen for the $\text{nRMSE}|_{exhale}^{exhale}$ and $E_n$ plots, which is explained by the coils' $B_1+$ variations predominately oriented along the anterior-posterior direction. However, solutions along this axis are susceptible towards respiration and the locations with optimal $\text{nRMSE}|_{half-inhale}^{exhale}$ and $\text{nRMSE}|_{inhale}^{exhale}$ show a clockwise twist with increasing half-inhale inhale respiration. The solution characterized by $k_r=0$ (both spokes are applied in excitation k-space center) is energy efficient with $E_n=12.1$ and $E_{max}=2.9$, but it shows with 11.9% the highest $\text{nRMSE}|_{exhale}^{exhale}$ value of all solutions. Including $\Delta B_0$ in optimization and Bloch simulation (right column) has only minor effect on the mean or median nRMSE values for the different respiratory positions To better characterize the potential impact of neglecting $\Delta B_0$ in pulse design, an additional case was considered, shown in FIG. 6c, where $\Delta B_0$ is not included in pulse optimization and, thus, $E_n$ and $E_{max}$ are identical to the left column in FIG. 6a, but $\Delta B_0$ is included in the Bloch simulations. Although a general increase of the mean and median values is observed, the different nRMSE polar plots resemble the results in FIG. 6a (right) with similar locations observed for the minima and maxima. The impact of respiration induced $\Delta B_0$ variations seems far less significant than that of the corresponding $|B_1^+|$ maps alterations.

Impact of Slice Orientation on 2-Spoke Pulses

Figure 7A:
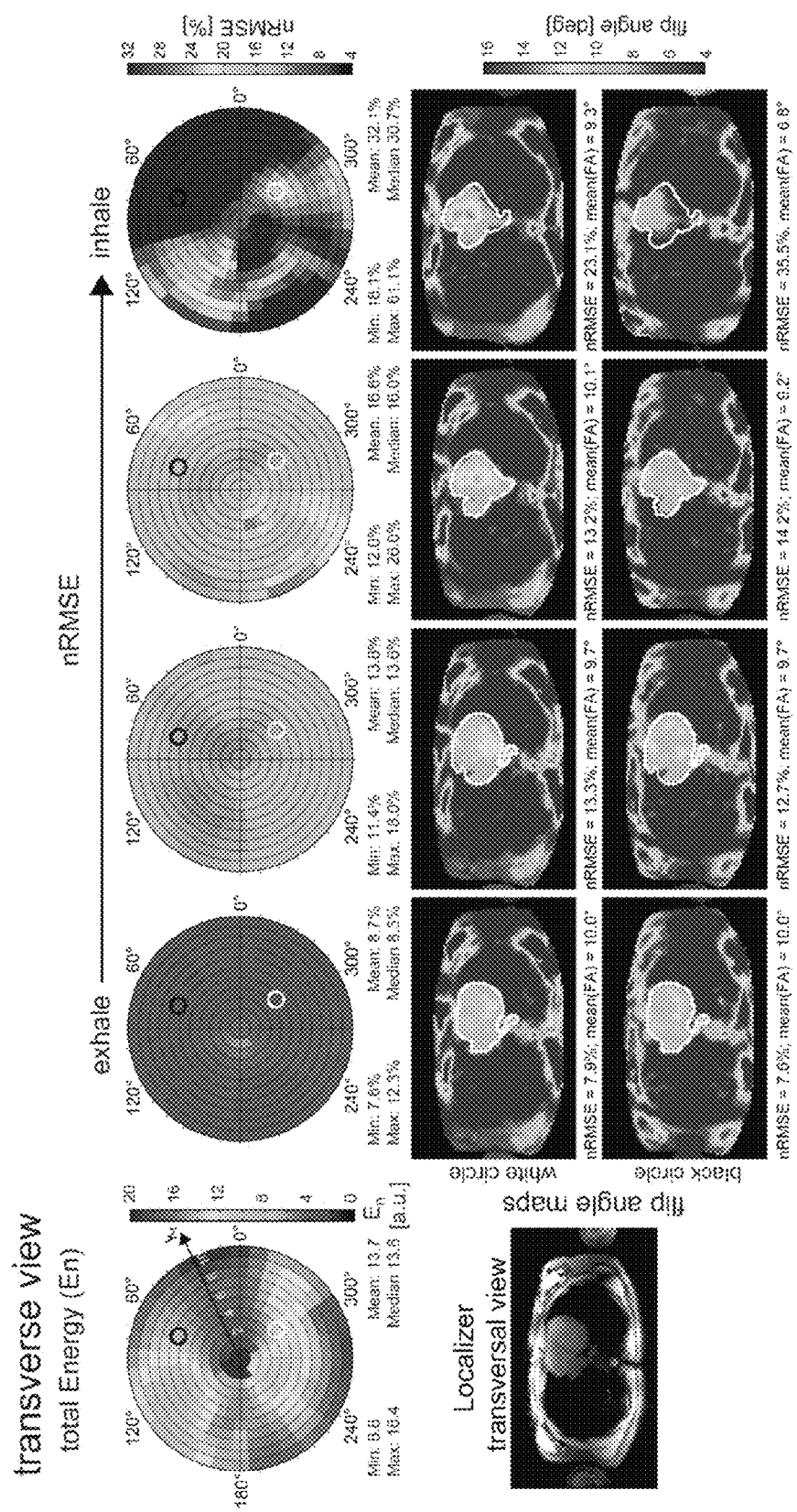
FIG. 7A is a report showing an impact of the respiratory position on the excitation fidelity for 2-spoke excitations optimized on exhale, respectively, for a transversal view.
Figure 7B:
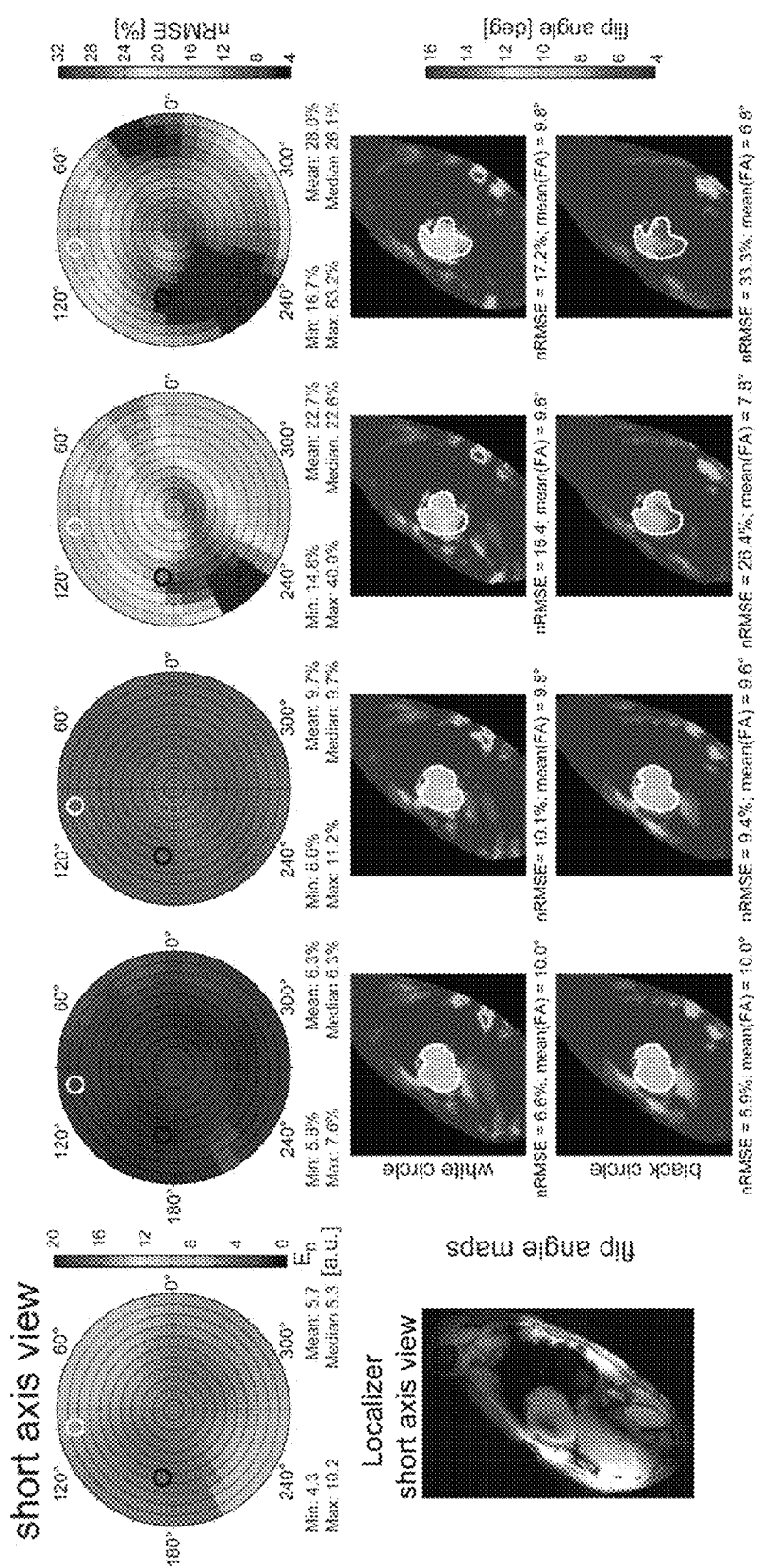
FIG. 7B is a report showing an impact of the respiratory position on the excitation fidelity for 2-spoke excitations optimized on exhale, respectively, for a short axis view.
Figure 7C:
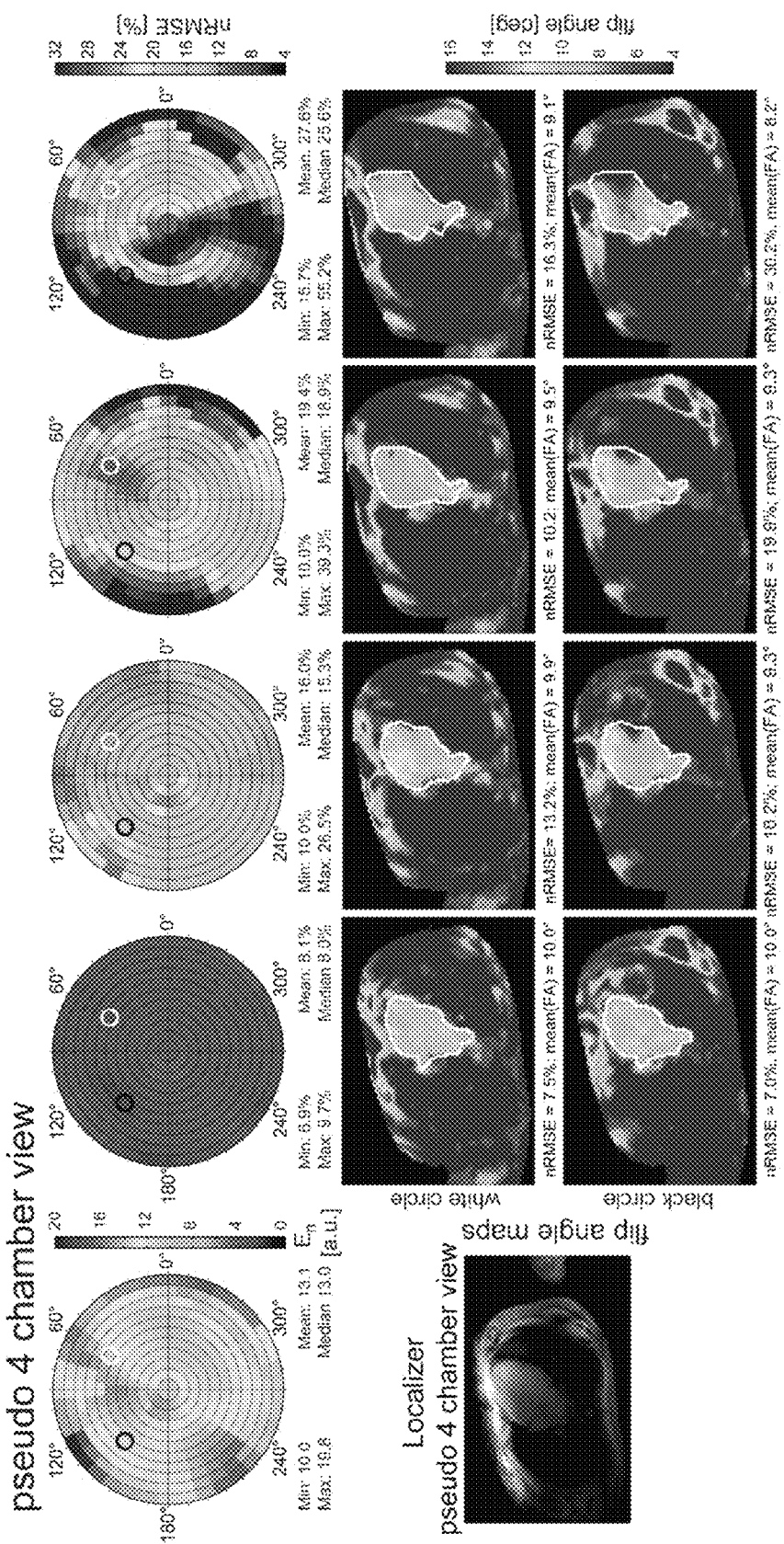
FIG. 7C is a report showing an impact of the respiratory position on the excitation fidelity for 2-spoke excitations optimized on exhale, respectively, for a pseudo four-chamber view.

FIG. 7 analyzes the impact of the spokes location on 3 different orientations in subject 2. For each view, En and nRMSE are illustrated in same coordinates as defined in FIG. 6B, and the nRMSE are shown for four different respiratory positions. For each view, two solutions (black and white circle) are chosen and corresponding Bloch simulations are illustrated for all four respiratory positions. The black circle marks solutions with $\mathrm{nRMSE}|_{exhale}^{exhale}$ values close to the minimum and acceptable En, but which are sensitive to changes in the respiratory position. In contrast, the white circle marks solutions that are most robust against respiration.

Again, optimization was based on calibration maps ($B_1^+$ and $\Delta B0$) obtained in exhale, respectively, and flip angle maps were calculated in this subject for 4 different respiratory positions between end-expiration and end-inhalation. In agreement with FIG. 6b, a continuous increase in the mean nRMSE value is observed with increasing respiratory volume for all views. In the transverse view, similar exhale $\mathrm{nRMSE}|_{exhale}^{exhale}$ mean values (8.7%) were obtained as in subject 1 shown in FIG. 6b (8.0%), which increase up to a mean value of 32.1% in subject 2 and 23.4% in subject 1. For each orientation in FIG. 7 two solutions are marked: i) black circle indicate exhale solutions with acceptable tradeoff between $\mathrm{nRMSE}|_{exhale}^{exhale}$ and $E_n$, the latter information was accessible in previous cardiac pTX RF pulse designs. The nRMSE of those solutions however show strong variation with respiratory position. ii) The white circle indicates solutions that are less optimal in terms of energy and/or $\mathrm{nRMSE}|_{exhale}^{exhale}$ than the black solution but more robust against respiration. Choosing those solutions, however, requires the knowledge of the nRMSE for all respiratory positions, which is usually not accessible. Bloch simulations are added in FIG. 7 for each of the two selected solutions together with corresponding nRMSE values and mean flip angle values. Comparing the Bloch simulations in the transverse view reveals a stronger increase of nRMSE and stronger reduction of the flip angle with increasing inhalation for the black solution ($\mathrm{nRMSE}|_{inhale}^{exhale}=35.5\%$, FA=6.8°) compared to the white solution ($\mathrm{nRMSE}|_{inhale}^{exhale}=32.1\%$ and mean FA=9.3°).

Similar observation can be made in short axis view although both, energy and $\mathrm{nRMSE}|_{exhale}^{exhale}$, show lower values as in transverse view, due to size and orientation of the optimization ROI. In this view, the black circle solution ($k_r=6$ m$^{-1}$, $\varphi=170°$) shows an $\mathrm{nRMSE}|_{exhale}^{exhale}$ value close to the minimum (5.9%) and a low $E_n$ of 4.4. Like in transverse view this preferable solution is particularly prone to respiration achieving an $\mathrm{nRMSE}|_{inhale}^{exhale}$ value of 33.3%. Instead the white solution ($k_r=9$ m$^{-1}$, $\varphi=100°$) achieves less optimal $E_n=6.6$ and $\mathrm{nRMSE}|_{exhale}^{exhale}=6.6\%$, but is less prone to respiration with $\mathrm{nRMSE}|_{inhale}^{exhale}=17.2\%$. Still, a local flip angle reduction in the inferior part of the ROI can be observed in the Bloch simulation for inhale. Results shown in pseudo 4 chamber view (FIG. 6c) are qualitatively and quantitatively comparable to the transverse view. For the black solution a band of reduced FA can be identified in the Bloch simulation for inhale position.

Robust and Conventional RF Pulse Design Applied In-Vivo

Figure 8A:
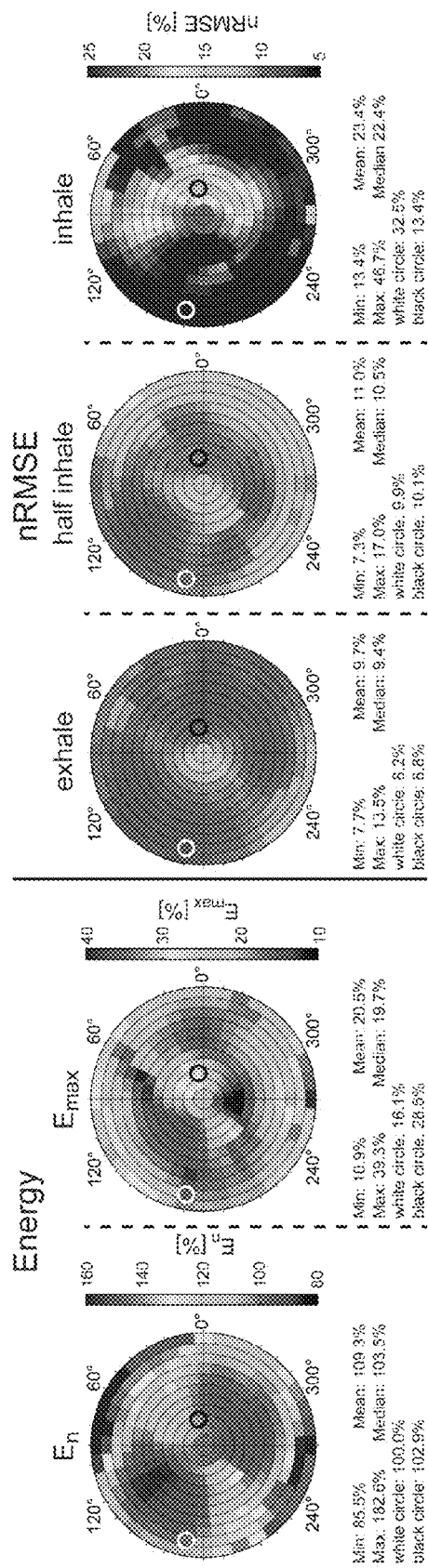
FIG. 8A a is a series of polar plots showing the standard 2-spoke RF pulse design, based on calibration maps obtained in exhale position.
Figure 8B:
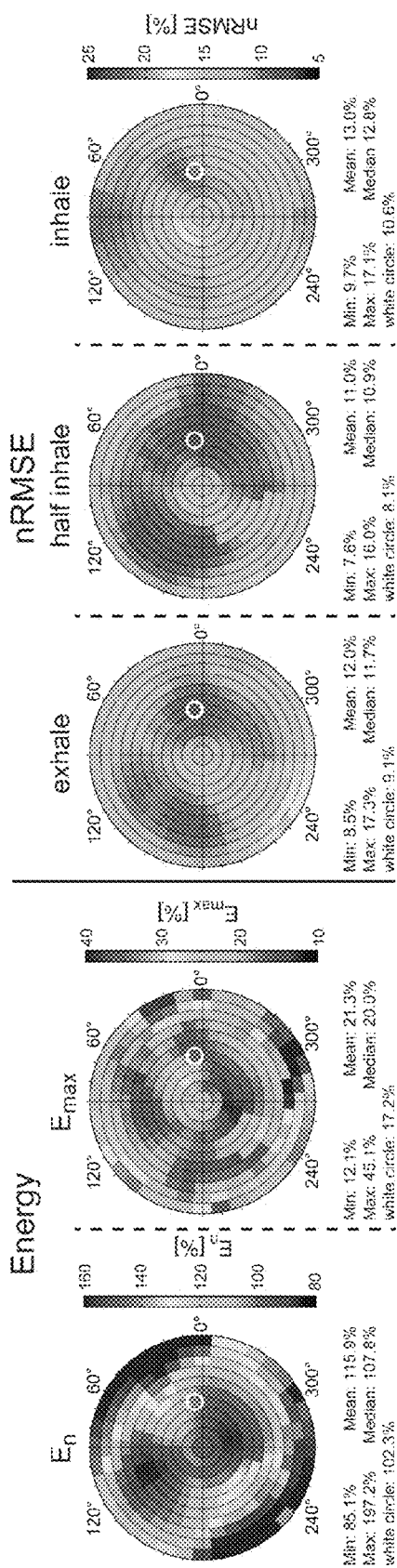
FIG. 8B a is a series of polar plots showing the proposed 2-spoke RF pulse design based on calibration maps obtained in exhale and inhale.
Figure 9A:
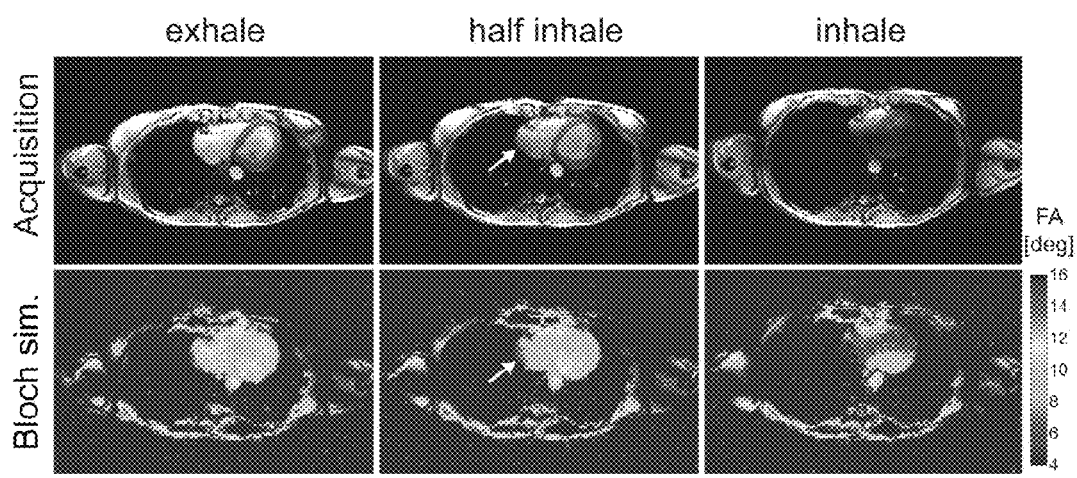
FIG. 9A is a series of images and corresponding Bloch simulations the standard 2-spoke RF pulse design.
Figure 9B:
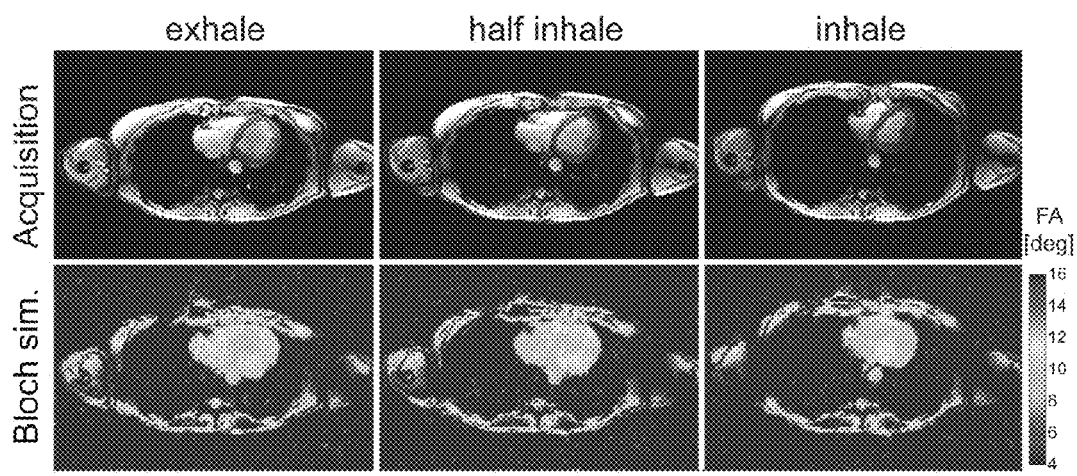
FIG. 9B is a series of images and corresponding Bloch simulations for the proposed the 2-spoke RF pulse design showing that it is robust against respiration and noting the corresponding solutions in FIGS. 8A and 8B.

FIG. 8 compares the optimization performed for subject 1 based on the traditional design with optimization based on exhale position (labeled "design I" in the following; FIG. 8a) and on the proposed RF pulse design (labeled "design II") which utilizes calibration maps obtained in exhale and inhale position simultaneously (FIG. 8b). Providing that a similar range of $E_n$ values is achieved by the two designs (left column; $E_n$ and $E_{max}$ are normalized to white circled solution in a), design II shows a general elevation of $\mathrm{nRMSE}|_{exhale}^{(exhale,inhale)}$ values with a mean of 12.0% compared to the exhale design I with a mean $\mathrm{nRMSE}|_{exhale}^{exhale}$ value of 9.7%. While nRMSE values for the latter design increase with increasing respiration, values for the design II remain fairly stable as listed in FIG. 8. For in-vivo comparison a single solution was chosen for each design. As design I utilizes calibration maps based on exhale position only, a favorable solution that trades between low $E_n$, $E_{max}$ and $\mathrm{nRMSE}|_{exhale}^{exhale}$ was chosen ($\mathrm{nRMSE}|_{half-inhale}^{exhale}$ and $\mathrm{nRMSE}|_{inhale}^{exhale}$ are assumed to be unknown). For design II, the choice also considers an acceptable nRMSE value for exhale and inhale while aiming to achieve same $E_n$ and $E_{max}$ values as in design I. Resulting Bloch simulations and corresponding in-vivo acquisitions are shown in FIG. 9 for both designs. While design I in FIG. 9a shows compromised image quality already for the half inhale position (see arrow) and strong image degradation for the inhale position, image contrast and homogeneity remains constant for design II with nRSME values of 9.1%/8.1%/10.6% for exhale/half inhale/inhale.

Discussion

The study in this example was designed to investigate the impact of respiration on cardiac RF pulse design using either 1-spoke (equivalent to $B_1^+$ shimming with phase and magnitude optimization) or 2-spoke pTX excitation. For this investigation $B_1^+$ and $B_0$ mapping sequences were modified in order to include interleaved navigator images of the diaphragm. However, as will be described, navigators are optional.

RF pulses are often designed based on one set of calibration maps obtained in a single physiological condition, including the respiratory position. When subsequently applied at different phases of the respiration cycle, such RF pulses can result in substantial deviations of the excitation pattern. We identified two predominant sources of respiration induced errors: i) the alteration of the $B_1^+$ profiles (magnitude and phase) of the transmit coil elements during the respiratory cycle, and ii) the use of small regularization weight in RF pulse optimization yielding higher excitation fidelity but relatively larger sensitivity to respiration quantified by $R_{exhale}^{inhale}$. Interestingly, respiration induced variations of $B_0$ only had a marginal impact on excitation patterns, even though they altered the optimal 2-spoke positions in excitation k-space. The same overall trend was observed for all orientations (transversal, short axis or four chamber view), with excitation pattern alterations already visible at half-inhale and more pronounced at inhale using conventional RF pulse design based on $B_1^+/B_0$ calibration at exhale. Similar results were obtained in all five subjects investigated in the study as listed in Table 1.

TABLE 1

Summary of nRMSE values with standard 2-spoke excitation in all subjects and all views

|  |  | Minimum nRMSE [%] | | | Maximum nRMSE [%] | | | Mean nRMSE [%] | | |
|---|---|---|---|---|---|---|---|---|---|---|
|  |  | Exh. | Half-Inh. | Inh. | Exh | Half-Inh. | Inh | Exh. | Half-Inh. | Inh. |
| Subject 1 | transversal | 7.7 | 7.3 | 13.4 | 13.5 | 17.0 | 46.7 | 9.7 | 11.0 | 23.4 |
|  | short axis | 7.8 | 7.0 | 13.3 | 12.5 | 23.3 | 56.4 | 8.6 | 10.4 | 24.5 |
|  | 4 chamber | 6.9 | 9.1 | 12.4 | 10.5 | 15.4 | 40.6 | 8.6 | 12.3 | 18.4 |
| Subject 2 | transversal | 7.6 | 11.4 | 18.1 | 12.3 | 18.0 | 61.1 | 8.7 | 13.8 | 32.2 |
|  | short axis | 5.8 | 8.0 | 16.7 | 7.6 | 11.2 | 63.2 | 6.3 | 9.7 | 28.0 |
|  | 4 chamber | 6.9 | 10.9 | 10.0 | 9.7 | 26.5 | 39.3 | 8.1 | 16.0 | 19.5 |
| Subject 3 | transversal | 6.7 | 13.1 | 15.7 | 16.3 | 36.1 | 48.2 | 9.7 | 21.9 | 28.7 |
|  | short axis | 6.1 | 10.4 | 17.0 | 12.3 | 37.7 | 64.8 | 7.9 | 17.2 | 29.1 |
|  | 4 chamber | 6.9 | 10.0 | 15.7 | 9.7 | 26.5 | 55.2 | 8.1 | 16.0 | 27.6 |
| Subject 4 | transversal | 7.0 | 9.1 | 10.7 | 10.5 | 20.3 | 32.0 | 8.4 | 12.8 | 17.7 |
|  | short axis | 7.8 | 11.3 | 17.7 | 12.1 | 19.7 | 38.2 | 8.9 | 13.8 | 26.1 |
|  | 4 chamber | 7.8 | 9.4 | 9.9 | 17.5 | 20.0 | 32.2 | 9.7 | 13.0 | 15.4 |
| Subject 5 | transversal | 8.5 | 18.4 | 18.5 | 15.9 | 44.7 | 56.4 | 9.8 | 27.3 | 31.3 |
|  | short axis | 8.5 | 14.4 | 15.7 | 14.4 | 42.3 | 52.0 | 10.5 | 23.6 | 28.1 |
|  | 4 chamber | 7.1 | 15.7 | 15.5 | 13.4 | 33.9 | 64.5 | 8.3 | 20.7 | 25.6 |

In Table 1, the RF pulses were optimized only based on the exhale state as indicated by gray shading. In subject 2, where 4 different respiratory positions were investigated, the middle columns (half-inhale) denote the respiratory position of 33% inhale.

Table 2 provides nRMSE values with 2-spoke excitation in all subjects and all views.

Table 2

Summary of nRMSE values with respiration robust 2-spoke excitation in all subjects and all views.

|  |  | Minimum nRMSE [%] | | | Maximum nRMSE [%] | | | Mean nRMSE [%] | | |
|---|---|---|---|---|---|---|---|---|---|---|
|  |  | Exh. | Half-Inh. | Inh. | Exh | Half-Inh. | Inh | Exh. | Half-Inh. | Inh. |
| Subject 1 | transversal | 7.4 | 8.7 | 7.3 | 10.8 | 16.4 | 11.9 | 8.8 | 10.8 | 8.8 |
|  | short axis | 5.8 | 6.4 | 7.0 | 8.8 | 14.4 | 10.1 | 6.8 | 9.0 | 7.9 |
|  | 4 chamber | 6.1 | 8.2 | 7.8 | 10.1 | 15.1 | 12.2 | 7.7 | 11.3 | 9.6 |
| Subject 2 | transversal | 7.6 | 11.5 | 10.0 | 15.2 | 19.8 | 17.4 | 10.5 | 14.6 | 13. |
|  | short axis | 5.1 | 7.3 | 7.4 | 9.9 | 12.6 | 13.2 | 6.0 | 9.1 | 8.8 |
|  | 4 chamber | 6.5 | 10.1 | 7.8 | 10.9 | 19.5 | 12.7 | 8.9 | 13.8 | 9.6 |
| Subject 3 | transversal | 5.9 | 9.7 | 8.7 | 14.0 | 26.1 | 18.7 | 8.5 | 16.5 | 11. |
|  | short axis | 6.1 | 7.7 | 6.4 | 17.8 | 26.9 | 16.7 | 7.8 | 12.5 | 10. |
|  | 4 chamber | 8.0 | 11.7 | 8.2 | 15.6 | 26.0 | 17.2 | 10.5 | 17.9 | 11. |
| Subject 4 | transversal | 5.5 | 7.1 | 7.4 | 9.8 | 15.5 | 12.1 | 7.1 | 10.1 | 9.5 |
|  | short axis | 5.3 | 7.0 | 6.6 | 10.9 | 12.7 | 10.3 | 6.8 | 9.6 | 8.2 |
|  | 4 chamber | 6.4 | 7.4 | 6.2 | 16.4 | 15.0 | 11.3 | 8.3 | 9.4 | 8.0 |
| Subject 5 | transversal | 11.0 | 14.5 | 10.1 | 21.6 | 26.9 | 17.7 | 12.7 | 17.6 | 13. |
|  | short axis | 9.7 | 11.9 | 8.4 | 18.3 | 30.1 | 19.8 | 12.1 | 15.1 | 12. |
|  | 4 chamber | 7.0 | 11.9 | 9.3 | 17.4 | 26.2 | 22.9 | 8.4 | 14.6 | 11. |

RF pulses were optimized using the robust pulse design based on both, the exhale and the inhale state, indicated by gray shading. In subject 2, where 4 different respiratory positions were investigated, the middle columns (half-inhale) denote the respiratory position of 33% inhale.

These excitation defects can significantly impact cardiovascular applications, as shown here in cardiac CINE acquisitions. Many of these applications rely on breath-hold acquisitions, and the observations indicate that, even with careful breath-hold instructions, significant variations of respiratory position may occur for some subjects between subsequent breath-holds, resulting in a mismatch between $B_1^+/B_0$ calibration and actual imaging scans. Instability between breath-holds is a known issue; one way to ensure excitation profile consistency is to include a navigator prior to the imaging scan and discard images based on the diaphragm position determined by the navigator. Alternatively, as will be described, different pTX RF pulses can be designed for different respiratory positions, and the actual RF pulse to be played out be determined by the navigator image collected prior to each imaging scan.

As described above and further outlined below, the present disclosure provides an approach using for RF pulse design that includes calibration maps obtained at multiple positions in a physiological cycle, such as multiple respiratory positions. These maps are assembled as a group of virtual slices that can be optimized simultaneously over the target region, resulting in pTX RF pulses robust against respiration induced errors. This design is not restricted to degradation caused by cyclical physiological motion, such as respiratory motion.

The framework described herein is not limited to spokes or slice selective pulses. It can be applied to 3D slab selective, localized or non-selective pTX RF pulses, as well as to simultaneous multi-slice pTX acquisitions ("pTX Multiband") demonstrated in cardiac CINE acquisitions at 7T. Furthermore, other regularization terms such as local or global SAR constraints can be included in the optimization.

It is known that respiration changes the heart position within the body. To follow heart motion with respiration, slice-tracking techniques are often applied based on the diaphragm position using a typical scaling factor of 0.6. In one subject, we investigated respiration induced excitation pattern changes including slice tracking with different factors between 0 and 1.5. Slice tracking did not significantly change the exhale polar plot pattern, however, nRMSE$|_{inhale}^{exhale}$ values overall tend to increase with increasing tracking factor.

Figure 10A:
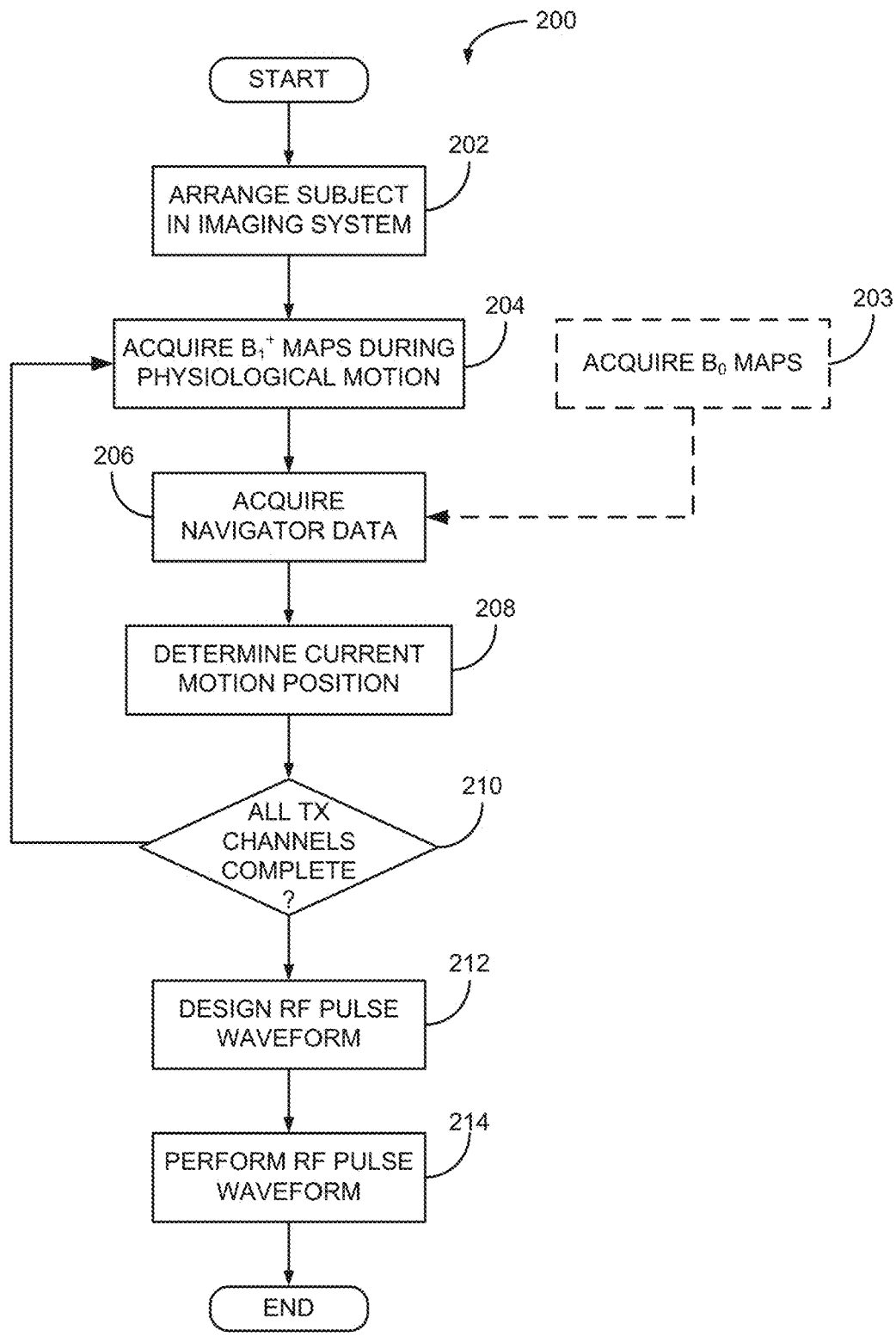
FIG. 10A is a flowchart setting forth examples of steps of a method in accordance with one aspect of the disclosure.

Referring to FIG. 10A, a flowchart is provided that sets forth some examples of steps 200 that may be performed for creating a pulse sequence using $B_1^+$ and, optionally $B_0$, mapping and including navigator images. The process begins at process block 202 with positioning the subject in an MR imaging system, for example, as described with respect to FIG. 1. Once positioned, at process block 204 the process continues by acquiring $B_1^+$ maps as physiological motion occurs. As one non-limiting example, the physiological motion may be reparatory motion. In this non-limiting example, the subject is permitted to breath freely. Also, optionally, as noted at process block 203, $B_0$ maps may be acquired. In this particular example, the mapping sequence runs, while the subject is asked to breath in and out deeply. The $B_1^+$ mapping acquisition for each TX channel is followed by a navigator scan at process block 206 that is used to determine, at process block 208, the current respiratory position. As one non-limiting example, the mapping for a single channel may be performed over one respiratory cycle, then mapping the next channel may be performed in the next respiratory cycle, and so on. In this example, a 16-channel TX system would utilize 16 respiratory cycles and, thus, take about 1-2 minutes scan time, depending on the respiration frequency. However, as a single mapping scan plus navigator does not require more than a few 100 milliseconds, 10 or more respiratory positions can be realized using this approach. Subsequently, the acquired maps can be binned retrospectively according to the measured navigator positions. Alternatively, an interactive scanning approach can be used, in which a direct feedback is provided to the scanner, whether the current scan falls into one of the (empty) bins and the measurements is not finished before all bins are filled.

In any case, at decision block 210, a check is made to determine if $B_1^+$ mapping has been performed for all channels. If not, the process iterates. Once $B_1^+$ mapping has been performed for all channels, at process block 212, the acquired information is used to design an RF pulse waveform that is robust against the physiological motion, such as respiratory motion, by designing the RF pulse waveform for specific states of physiological motion. That is, the B1+ calibration maps and, if optionally included, the $B_0$ maps, provided for the specific states of physiological motion are used to create an RF pulse waveform that is robust to the physiological motion of the subject, which in this non-limiting example, is respiratory motion. At process block 214, the RF pulse waveform is used to direct the MRI system to produce an RF field based on the designed RF pulse waveform. More particularly, the one or more maps can be assembled as a group of virtual slices that can be optimized simultaneously over the target region, such as described above, resulting in pTX RF pulses robust against errors caused by cyclical physiological motion, such as respiratory motion.

Figure 10B:
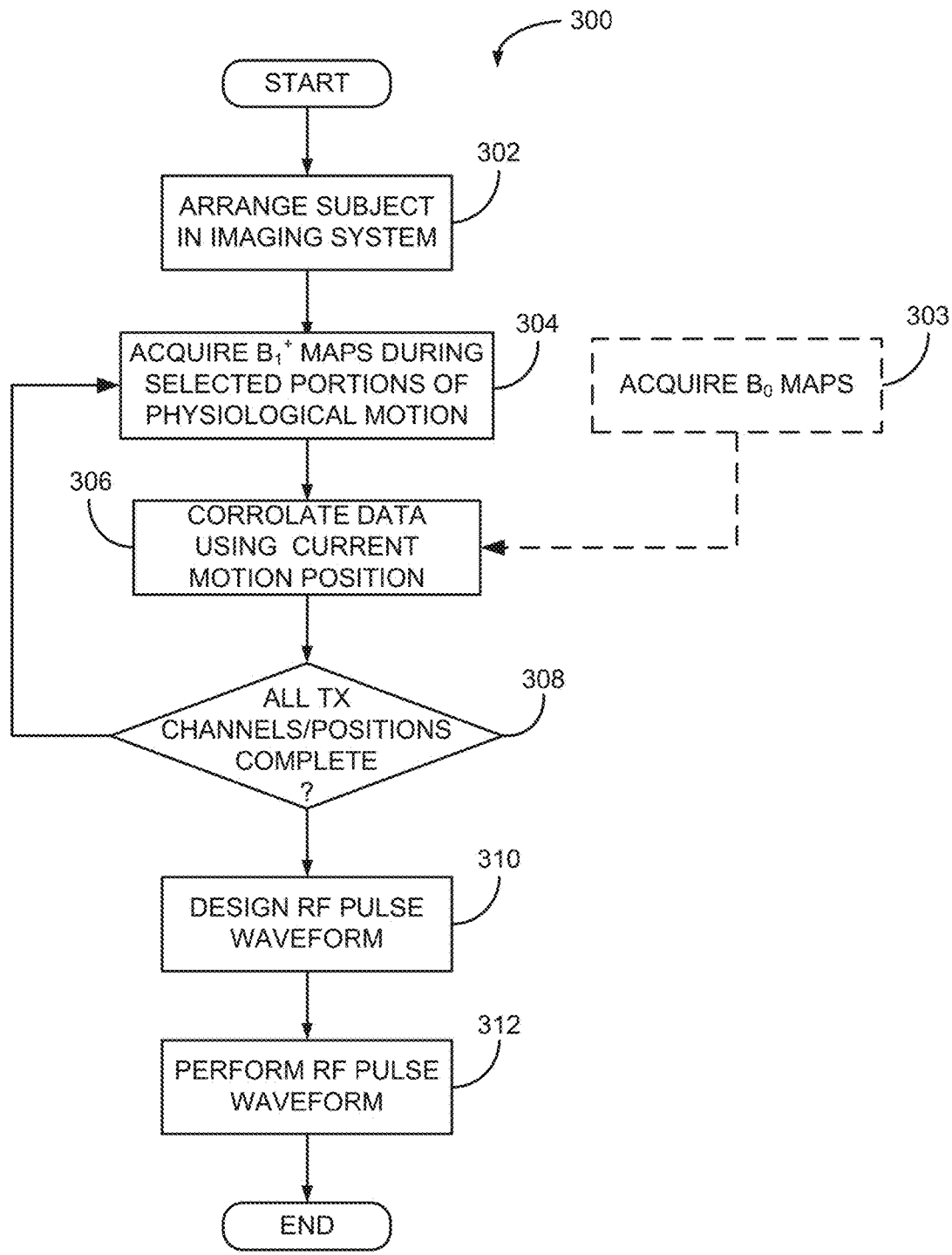
FIG. 10B is a flowchart setting forth examples of steps of a method in accordance with one aspect of the disclosure.

Referring now to FIG. 10B, mapping the $B_1^+$ field of different respiratory positions may also be performed without the use of a navigator sequence or acquisition of navigator data. Specifically, a process that does not include the use of navigators 300 begins at process block 302 with positioning the subject in the imaging system. At process block 304, $B_1^+$ maps are acquired for a few different states of the physiological motion. As a non-limiting example, the physiological motion may be respiratory motion and data is acquired at a selected points in the respiratory cycle during breath-holds. Also, optionally, $B_0$ maps may be acquired at process block 303. At process block 306, the acquired data is correlated or binned based on physiological position during acquisition. As a non-limiting example, $B_1^+$ maps for two extreme respiratory states, such as the "exhale" position and the "full inhale" position, can be obtained. The subject may be asked to hold the breath at the first respiratory position (e.g., exhale) during the $B_1^+$ mapping acquisition, which may have typical scan durations of 15-20 seconds for a 16 channel transmit system. At decision block 308, the scan is then repeated for each physiological position. If desired, the physiological positions can be monitored visually or by using a physiological monitoring systems, such as respiratory bellows, optical positioning monitors, and the like.

Once $B_1^+$ mapping has been performed for all channels and physiological positions, at process block 310, the acquired information is used to design an RF pulse waveform that is robust against the physiological motion, such as respiratory motion, by designing the RF pulse waveform for specific states of physiological motion. That is, the B1+ calibration maps and, if optionally included, the $B_0$ maps, provided for the specific states of physiological motion are used to create an RF pulse waveform that is robust to the physiological motion of the subject, which in this non-limiting example, is respiratory motion. At process block 312, the RF pulse waveform is used to direct the MRI system to produce an RF field based on the designed RF pulse waveform. More particularly, the one or more maps can be assembled as a group of virtual slices that can be optimized simultaneously over the target region, such as described above, resulting in pTX RF pulses robust against errors caused by cyclical physiological motion, such as respiratory motion.

The systems and methods of the present disclosure can also be applied to other (periodic) changes of the physiological state that alter $B_1^+$ maps. That is, as described herein this formalism has been applied on respiration robust 1-spoke cardiac imaging and expanded to 2-spoke pTX pulses that have been shown to be capable of improving further image homogeneity at 7T. The 1-spoke excitation can be initialized with different starting phase patterns, as can the 2-spoke excitations, such as with symmetric placement in k-space. This symmetric k-space approach, which has demonstrated high quality cardiac images at 7T, offers the advantage of being less sensitive if the RF pulses are scaled to larger FA and allows a straightforward visualization of optimization results as a function of spoke positions. However, the presented method is not restricted to a symmetric placement of the RF spokes; also, an asymmetric spoke placement, as well as more than 2 spokes can be used. It should be noted, however, that lower numbers of spokes are often preferable because cardiac RF pulses are typically fairly short and RF pulses durations from the vendor-standard sequences are between 0.6 ms and 2 ms, which becomes increasingly challenging to achieve with rising number of spokes.

As stated, the proposed RF pulse design is not limited to breath-hold applications. In practice, a variety of medical conditions preclude single or multiple breath-holds scans and therefore acquisitions are performed under free breathing. This is the case, for example, in children with congenital heart disease and in patients with arrhythmia who may not able to perform breath-holds, as well as in some elderly people who may have difficulties hearing breath-hold instructions. For these patients, the proposed algorithm can be used to improve image quality, based on the modified calibration scans, for example, with navigator images prior to each image, compatible with free-breathing as well. In the latter case, calibration maps could be acquired during a few training breathing cycles and retrospectively reordered according to the respiratory position or prospectively acquired using the navigator image information. In other clinical situations, active respiration is desirable for diagnostic purpose. In constrictive pericardial disease, pathological ventricular coupling can lead to an abnormal motion or bending of the septum, which is highly dependent on respiration, requiring fast 2D acquisitions to be performed while the patient is asked to breathe deeply in and out. For these acquisitions, reduction of the FA and impaired contrast homogeneity may be expected as demonstrated in this study.

Besides patient restrictions, many sequences cannot be performed during breath-hold due to long scan times. Commonly those acquisitions use respiration navigator tracking that discard images that are outside the navigator acceptance window which typically achieve acceptance efficiencies between 30-50%. However, recently there have been significant advances in increasing 2D or 3D scan efficiency up to 100% (i.e. using data of the entire respiratory cycle) for coronary MRA, cardiac perfusion or cardiac CINE acquisitions, while prospectively or retrospectively correcting for respiratory motion. Some have reported a 3D cardiac $T_1$ mapping approach that uses 100% scan efficiency for outer k-space lines and a reduced efficiency on the inner k-space part. Furthermore, improved hardware and novel acceleration techniques contribute to enable free-breathing real-time cardiac imaging with temporal resolutions below 50 ms as demonstrated by several groups.

Notably, even at 3T, heterogeneous $B_1^+$ and $B_0$ patterns can significantly impact image quality, which has resulted in the recent development of clinical 3T pTX scanners operating now with 2 transmit channels, with improved flip angle homogeneity for cardiac applications. Thus, the systems and methods of the present disclosure can also be highly valuable at lower field strengths. In the context of UHF, where CMR can benefit from longer $T_1$ relaxation, higher SNR and better parallel imaging performance, addressing respiratory induced excitation profile degradations with the proposed robust RF pulse design is expected to have a substantial impact on potential clinical outcome.

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system comprising:
   a magnet system configured to generate a polarizing magnetic field about at least a region of interest (ROI) of a subject arranged in the MRI system, the ROI being subject to cyclical physiological motion including a plurality of different states of physiological motion;
   a plurality of gradient coils configured to apply a gradient field with respect to the polarizing magnetic field;
   a radio frequency (RF) system configured to apply RF excitation fields to the subject and acquire MR image data therefrom; and
   a computer programmed to:
     acquire a $B_1^+$ calibration map for each of a plurality of selected ones of the plurality of different states of physiological motion in the subject, wherein each $B_1^+$ calibration map is correlated with a state of the physiological motion in the subject during acquisition of the $B_1^+$ calibration map;
     using the $B_1^+$ calibration maps and correlated state of the physiological motion in the subject, design an RF pulse waveform that reduces B1+ inhomogeneity at each correlated state of physiological motion;
     control the plurality of gradient coils and the RF system to produce an RF field based on a portion of the RF pulse waveform to acquire the image data from the subject, wherein the portion of the RF pulse waveform is correlated with a state of physiological motion of the subject during acquisition of the image data; and
     reconstruct an image of the subject from the image data.

2. The MRI system of claim 1, wherein the computer is further programmed to track a state of the physiological motion in the subject without performing a navigator pulse sequence.

3. The MRI system of claim 1, wherein the computer is further programmed to assemble the $B_1^+$ calibration maps into groups of virtual slices within the ROI and, to design the RF pulse waveform, the computer is further programmed to simultaneously design the RF pulse waveform using the groups of virtual slices to reduce errors induced by the physiological motion in the ROI.

4. The MRI system of claim 3, wherein the computer is further programmed to simultaneously optimize the RF pulse waveform using the groups of virtual slices to minimize errors induced by the physiological motion in the ROI.

5. The MRI system of claim 1, wherein the computer is further programmed to design the RF pulse waveform as a parallel transmission RF pulse waveform.

6. The MRI system of claim 1, wherein the computer is further programmed to acquire $B_0$ calibration maps for each of a plurality of different states of physiological motion in a subject and use the $B_0$ calibration maps to design the RF pulse waveform.

7. The MRI system of claim 1, wherein the physiological motion is respiratory motion.

* * * * *

UNITED STATES PATENT AND TRADEMARK OFFICE
CERTIFICATE OF CORRECTION

PATENT NO. : 10,247,803 B2
APPLICATION NO. : 14/696099
DATED : April 2, 2019
INVENTOR(S) : Sabastian Schmitter et al.

It is certified that error appears in the above-identified patent and that said Letters Patent is hereby corrected as shown below:

In the Specification

Column 7, Line 53, Eq. [1], "$\hat{b} = \arg\min\left(\||Ab|-|m|\|_w^2 + R(b)\right)$" should be $$\hat{\mathbf{b}} = \arg\min\left(\||\mathbf{Ab}|-|\mathbf{m}|\|_w^2 + R(\mathbf{b})\right)$$.

Column 8, Line 33, Eq. [4], "$\alpha(r)|_{P_{actual}}^{P_{refernece}} = f_{Bloch}\left(\hat{b}|_{P_{reference}}, B_{l,k}^+|_{P_{actual}}, \Delta B_0|_{P_{actual}}\right)$"

should be -- $\alpha(r)|_{P_{actual}}^{P_{reference}} = f_{Bloch}\left(\hat{b}|_{P_{refernece}}, B_{l,k}^+|_{P_{actual}}, \Delta B_0|_{P_{actual}}\right)$ --.

Column 8, Line 41, "$\alpha(r)|_{exhale}^{exhale}$, $\alpha(r)|_{half-inhale}^{exhale}$ and $\alpha(r)|_{inhale}^{exhale}$" should be -- $\alpha(r)|_{exhale}^{exhale}$, $\alpha(r)|_{half-inhale}^{exhale}$ and $\alpha(r)|_{inhale}^{exhale}$ --.

Column 9, Line 2, "$a(r)|_{P_{actual}}^{P_{refernece}}$" should be -- $\alpha(r)|_{P_{actual}}^{P_{reference}}$ --.

Column 9, Line 7, "$a(r)|_{exhale}^{(exhale,inhale)}$" should be -- $\alpha(r)|_{exhale}^{(exhale,inhale)}$ --.

Column 9, Line 8, "$a(r)|_{half-inhale}^{(exhale,inhale)}$" should be -- $\alpha(r)|_{half-inhale}^{(exhale,inhale)}$ --.

Column 9, Line 8, "$a(r)|_{inhale}^{(exhale,inhale)}$" should be -- $\alpha(r)|_{inhale}^{(exhale,inhale)}$ --.

Signed and Sealed this
Twenty-first Day of May, 2019

Andrei Iancu
*Director of the United States Patent and Trademark Office*

CERTIFICATE OF CORRECTION (continued)
U.S. Pat. No. 10,247,803 B2

Column 13, Line 33, "$a(r)|_{P_{actual}}^{Prefernece}$" should be --$\alpha(r)|_{P_{actual}}^{Preference}$--.

Column 13, Line 48, "$a(r)|_{exhale}^{exhale}$" should be --$\alpha(r)|_{exhale}^{exhale}$--.

Column 13, Line 49, "$a(r)|_{exhale}^{(exhale,inhale)}$" should be --$\alpha(r)|_{exhale}^{(exhale,inhale)}$--.

Column 13, Line 50, "$a(r)|_{inhale}^{(exhale,inhale)}$" should be --$\alpha(r)|_{inhale}^{(exhale,inhale)}$--.

Column 13, Line 54, "$nRMSE|_{exhale}^{exhale}$" should be --$nRMSE|_{exhale}^{exhale}$--.

Column 13, Line 56, "$nRMSE|_{exhale}^{exhale}$" should be --$nRMSE|_{exhale}^{exhale}$--.

Column 15, Line 31, "$nRMSE|_{exhale}^{exhale}$" should be --$nRMSE|_{exhale}^{exhale}$--.

Column 15, Line 42, "$nRMSE|_{exhale}^{exhale}$" should be --$nRMSE|_{exhale}^{exhale}$--.

Column 15, Line 44, "$nRMSE|_{half-inhale}^{exhale}$" should be --$nRMSE|_{half-inhale}^{exhale}$--.

Column 15, Line 44, "$nRMSE|_{inhale}^{exhale}$" should be --$nRMSE|_{inhale}^{exhale}$--.

Column 15, Line 46, "$nRMSE|_{half-inhale}^{exhale}$" should be --$nRMSE|_{half-inhale}^{exhale}$--.

Column 15, Lines 46-47, "$nRMSE|_{inhale}^{exhale}$" should be --$nRMSE|_{inhale}^{exhale}$--.

Column 15, Line 47, "$nRMSE|_{exhale}^{exhale}$" should be --$nRMSE|_{exhale}^{exhale}$--.

Column 15, Line 53, "$R_{exhale}^{half-inhale}$" should be --$R_{exhale}^{half-inhale}$--.

Column 15, Line 54, "$R_{exhale}^{inhale}$" should be --$R_{exhale}^{inhale}$--.

Column 15, Line 58, "$nRMSE|_{exhale}^{exhale}$" should be --$nRMSE|_{exhale}^{exhale}$--.

Column 15, Line 61-62, "$nRMSE|_{exhale}^{exhale}$" should be --$nRMSE|_{exhale}^{exhale}$--.

Column 15, Line 64-65, "$nRMSE|_{exhale}^{exhale}$" should be --$nRMSE|_{exhale}^{exhale}$--.

CERTIFICATE OF CORRECTION (continued)

Column 16, Line 2, "$R_{exhale}^{half-inhale}$" should be -- $R_{exhale}^{half-inhale}$ --.

Column 16, Line 3, "$R_{exhale}^{inhale}$" should be -- $R_{exhale}^{inhale}$ --.

Column 16, Line 3, "$nRMSE|_{exhale}^{exhale}$" should be -- $nRMSE|_{exhale}^{exhale}$ --.

Column 16, Line 7, "$nRMSE|_{exhale}^{exhale}$" should be -- $nRMSE|_{exhale}^{exhale}$ --.

Column 16, Line 9, "$R_{exhale}^{half-inhale}$" should be -- $R_{exhale}^{half-inhale}$ --.

Column 16, Line 10, "$R_{exhale}^{inhale}$" should be -- $R_{exhale}^{inhale}$ --.

Column 16, Line 10, "$R_{exhale}^{inhale}$" should be -- $R_{exhale}^{inhale}$ --.

Column 16, Line 13, "$nRMSE|_{exhale}^{exhale}$" should be -- $nRMSE|_{exhale}^{exhale}$ --.

Column 16, Line 14, "$R_{exhale}^{inhale}$" should be -- $R_{exhale}^{inhale}$ --.

Column 16, Line 15, "$nRMSE|_{exhale}^{exhale}$" should be -- $nRMSE|_{exhale}^{exhale}$ --.

Column 16, Line 15, "$R_{exhale}^{inhale}$" should be -- $R_{exhale}^{inhale}$ --.

Column 16, Line 19, "$R_{exhale}^{hafl-inhale} = 1.7, R_{exhale}^{inhale} = 3.9$" should be -- $R_{exhale}^{hafl-inhale} = 1.7, R_{exhale}^{inhale} = 3.9$ --.

Column 16, Line 20, "$nRMSE|_{exhale}^{exhale}$" should be -- $nRMSE|_{exhale}^{exhale}$ --.

Column 16, Line 22, "$nRMSE|_{exhale}^{exhale}$" should be -- $nRMSE|_{exhale}^{exhale}$ --.

Column 16, Line 23, "$nRMSE|_{inhale}^{exhale}$" should be -- $nRMSE|_{inhale}^{exhale}$ --.

Column 16, Line 28, "$nRMSE|_{exhale}^{exhale}$" should be -- $nRMSE|_{exhale}^{exhale}$ --.

Column 16, Line 51, "$nRMSE|_{exhale}^{exhale}$" should be -- $nRMSE|_{exhale}^{exhale}$ --.

CERTIFICATE OF CORRECTION (continued)
U.S. Pat. No. 10,247,803 B2

Column 16, Line 55, "$nRMSE\,|_{half-inhale}^{exhale}$" should be -- $nRMSE\,|_{half-inhale}^{exhale}$ --.

Column 16, Line 55, "$nRMSE\,|_{inhale}^{exhale}$" should be -- $nRMSE\,|_{inhale}^{exhale}$ --.

Column 16, Line 60, "$nRMSE\,|_{exhale}^{exhale}$" should be -- $nRMSE\,|_{exhale}^{exhale}$ --.

Column 17, Line 19, "$nRMSE\,|_{exhale}^{exhale}$" should be -- $nRMSE\,|_{exhale}^{exhale}$ --.

Column 17, Line 31, "$nRMSE\,|_{exhale}^{exhale}$" should be -- $nRMSE\,|_{exhale}^{exhale}$ --.

Column 17, Line 36, "$nRMSE\,|_{exhale}^{exhale}$" should be -- $nRMSE\,|_{exhale}^{exhale}$ --.

Column 17, Line 41, "$nRMSE\,|_{exhale}^{exhale}$" should be -- $nRMSE\,|_{exhale}^{exhale}$ --.

Column 17, Line 50, "$nRMSE\,|_{inhale}^{exhale}$" should be -- $nRMSE\,|_{inhale}^{exhale}$ --.

Column 17, Line 52, "$nRMSE\,|_{inhale}^{exhale}$" should be -- $nRMSE\,|_{inhale}^{exhale}$ --.

Column 17, Line 54, "$nRMSE\,|_{exhale}^{exhale}$" should be -- $nRMSE\,|_{exhale}^{exhale}$ --.

Column 17, Line 57, "$nRMSE\,|_{exhale}^{exhale}$" should be -- $nRMSE\,|_{exhale}^{exhale}$ --.

Column 17, Line 60, "$nRMSE\,|_{inhale}^{exhale}$" should be -- $nRMSE\,|_{inhale}^{exhale}$ --.

Column 17, Line 62, "$nRMSE\,|_{exhale}^{exhale}$" should be -- $nRMSE\,|_{exhale}^{exhale}$ --.

Column 17, Line 64, "$nRMSE\,|_{inhale}^{exhale}$" should be -- $nRMSE\,|_{inhale}^{exhale}$ --.

Column 18, Line 16, "$nRMSE\,|_{exhale}^{(exhale,inhale)}$" should be -- $nRMSE\,|_{exhale}^{(exhale,inhale)}$ --.

Column 18, Line 18, "$nRMSE\,|_{exhale}^{exhale}$" should be -- $nRMSE\,|_{exhale}^{exhale}$ --.

Column 18, Line 24, "$nRMSE\,|_{exhale}^{exhale}$" should be -- $nRMSE\,|_{exhale}^{exhale}$ --.

Column 18, Line 25, "$nRMSE\,|_{half-inhale}^{exhale}$" should be -- $nRMSE\,|_{half-inhale}^{exhale}$ --.

CERTIFICATE OF CORRECTION (continued)
U.S. Pat. No. 10,247,803 B2

Column 18, Line 25, "$nRMSE\,|_{inhale}^{exhale}$" should be -- $nRMSE\,|_{inhale}^{exhale}$ --.

Column 18, Line 58, "$nRMSE\,|_{exhale}^{inhale}$" should be -- $nRMSE\,|_{exhale}^{inhale}$ --.